US012594280B2

(12) United States Patent
Rosa-Calatrava et al.

(10) Patent No.: US 12,594,280 B2
(45) **Date of Patent: *Apr. 7, 2026**

(54) ANTIVIRAL COMPOSITIONS FOR TREATING THE FLU

(71) Applicants: UNIVERSITE CLAUDE BERNARD LYON 1, Villeurbanne (FR); INSTITUT NATIONAL DE LA SANTE ET DE LA RECHERCHE MEDICALE (INSERM), Paris (FR); HOSPICES CIVILS DE LYON, Lyons (FR); UNIVERSITE LAVAL, Quebec (CA)

(72) Inventors: Manuel Rosa-Calatrava, Lyons (FR); Olivier Terrier, Lyons (FR); Julien Textoris, Villeurbanne (FR); Guy Boivin, Quebec (CA); Mario Pizzorno, Quebec (CA)

(73) Assignees: UNIVERSITE CLAUDE BERNARD LYON 1, Villeurbanne (FR); INSTITUT NATIONAL DE LA SANTE ET DE LA RECHERCHE MEDICALE (INSERM), Paris (FR); HOSPICES CIVILS DE LYON, Lyons (FR); UNIVERSITE LAVAL, Quebec (CA)

( * ) Notice: Subject to any disclaimer, the term of this patent is extended or adjusted under 35 U.S.C. 154(b) by 841 days.

This patent is subject to a terminal disclaimer.

(21) Appl. No.: 17/828,245

(22) Filed: May 31, 2022

(65) Prior Publication Data

US 2022/0296606 A1 Sep. 22, 2022

Related U.S. Application Data

(63) Continuation-in-part of application No. 15/557,170, filed as application No. PCT/EP2016/056036 on Mar. 18, 2016, now Pat. No. 11,351,180.

(30) Foreign Application Priority Data

Mar. 19, 2015 (FR) ...................................... 1552284

(51) Int. Cl.

| | |
|---|---|
| ***A61K 31/55*** | (2006.01) |
| ***A61K 9/00*** | (2006.01) |
| ***A61K 31/13*** | (2006.01) |
| ***A61K 31/196*** | (2006.01) |
| ***A61K 31/215*** | (2006.01) |
| ***A61K 31/4025*** | (2006.01) |
| ***A61K 31/665*** | (2006.01) |
| ***A61K 45/06*** | (2006.01) |
| ***A61P 31/16*** | (2006.01) |

(52) U.S. Cl.

CPC ............ *A61K 31/55* (2013.01); *A61K 9/0073* (2013.01); *A61K 31/13* (2013.01); *A61K 31/196* (2013.01); *A61K 31/215* (2013.01); *A61K 31/4025* (2013.01); *A61K 31/665* (2013.01); *A61K 45/06* (2013.01); *A61P 31/16* (2018.01)

(58) Field of Classification Search

CPC .............. A61K 31/554; A61K 31/5383; A61K 31/506; A61K 31/53; A61P 31/16; A61P 31/12

See application file for complete search history.

(56) References Cited

U.S. PATENT DOCUMENTS

| | | | |
|---|---|---|---|
| 4,605,552 | A | 8/1986 | Fritschi |
| 4,663,354 | A | 5/1987 | Niederhauser et al. |

FOREIGN PATENT DOCUMENTS

| | | | |
|---|---|---|---|
| CA | 2853715 | A1 | 5/2013 |
| EP | 0162320 | A1 | 11/1985 |
| EP | 0355395 | B1 | 2/1990 |
| EP | 0450705 | A1 | 10/1991 |
| EP | 0561861 | A1 | 3/1995 |
| EP | 0728751 | A2 | 8/1996 |
| EP | 1970061 | A1 | 9/2008 |
| FR | 2953410 | A1 | 12/2009 |
| JP | 2010-521480 | A | 6/2010 |
| WO | WO8707508 | A1 | 12/1987 |
| WO | WO2002094238 | A1 | 11/2002 |
| WO | WO2005007082 | A2 | 1/2005 |
| WO | WO2005102353 | A1 | 11/2005 |
| WO | 2007/101111 | A2 | 9/2007 |
| WO | 2008112775 | A1 | 9/2008 |
| WO | WO2011126071 | A1 | 10/2011 |

OTHER PUBLICATIONS

Chen et al., Targets for anti-influenza virus agents: research advances, J Int Pharm Res, 2013, 40(1), 1-7.

Jossett et al., Gene Expression Signature-Based Screening Identifies New Broadly Effective Influenza A Antivirals, PLoS ONE 5(10): e13169. 1-18.

Terrier et al., Host microRNA molecular signatures associated with human H1N1 and H3N2 influenza A viruses reveal an unanticipated antiviral activity for miR-146a, Journal of General Virology (2013), 94, 985-995.

Terrier et al., Cellular transcriptional profiling in human lung epithelial cells infected by different subtypes of influenza A viruses reveals an overall down-regulation of the host p53 pathway, Virology Journal 2011, 8:285, 1-11.

Wang et al: "Multiple system atrophy manifested as dizziness and imbalance: a report of two cases", European Archives of Oto-Rhino-Laryngology, Official Journal of the European Federation of Oto-Rhino-Laryngological Societies (EUFOS) : Affiliated With the German Society for Oto-Rhino-Laryngology-Head and Neck Surgery, vol. 260, No. 7, (Aug. 1, 2003), pp. 404-407.

(Continued)

*Primary Examiner* — Bahar Craigo

(74) *Attorney, Agent, or Firm* — Arrigo, Lee, Guttman & Mouta-Bellum LLP

(57) ABSTRACT

The present invention relates to a pharmaceutical or veterinary composition for the use thereof in preventing and/or treating infection by the influenza viruses. The composition is characterized in that it contains, in an appropriate pharmaceutical carrier, at least one compound selected from among Etilefrine and Diltiazem.

10 Claims, 18 Drawing Sheets

(56) References Cited

OTHER PUBLICATIONS

Spahr et al: "Tolcapone-related fulminant hepatitis: electron microscopy shows mitochondrial alterations", Digestive diseases and sciences, vol. 45, No. 9 (Sep. 2000), pp. 1881-1884.
Iacoangeli et al: "The ionophore 8,14 monensin inhibits mouse polyomavirus DNA replication and destabilizes viral early mRNAs", BIOCHIMIE, vol. 82, No. 1, (Jan. 1, 2000), pp. 35-39.
Holodniy et al: "Influenza treatment 10 and prophylaxis with neuraminidase inhibitors: a review", Infection and Drug Resistance, (Nov. 1, 2013), p. 187-198.
European Patent Office, International Search Repor in PCT/EP2016/056036, Sep. 6, 2016.
Chen, Wei, et al., "Targets for anti-influenza virus agents: research advances," J. Int. Pharm. Res., vol. 40, No. 1, 1-7 (2013).
English translation of Office Action dated Feb. 3, 2020, in Chinese Application No. 201600165745.
Notice of Reasons for Rejection, Japanese Application No. 2017-567547, mailed Jul. 20, 2020.
McCullers, The Journal of Infectious Diseases, "Effect of Antiviral Treatment on the Outcome of Secondary Bacterial Pneumonia after Influenza", 2004, vol. 190, pp. 519-526.
Nguyen et al., PLoS ONE, "Efficacy of Combined Therapy with Amantadine, Oseltamivir, and Ribacarin In Vivo against Susceptible and Amantadine-Resistant Influenza A Viruses", 2011, vol. 7, No. 1, e31006 (9 pages).

Figure 3A Etilefrine
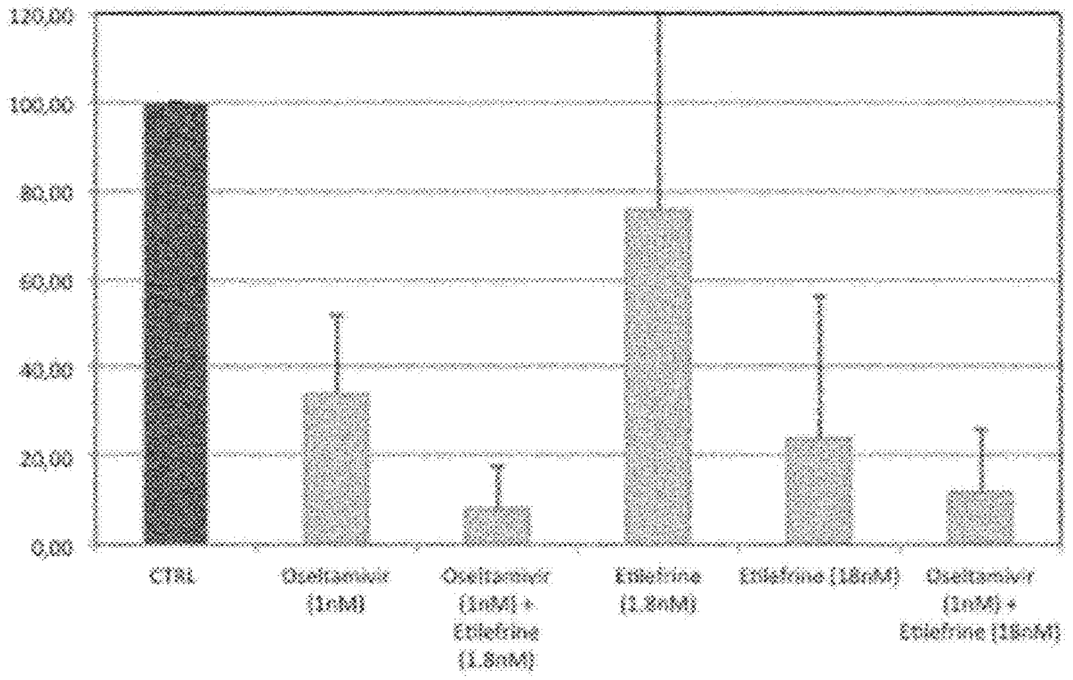
Figure 3B Diltiazem
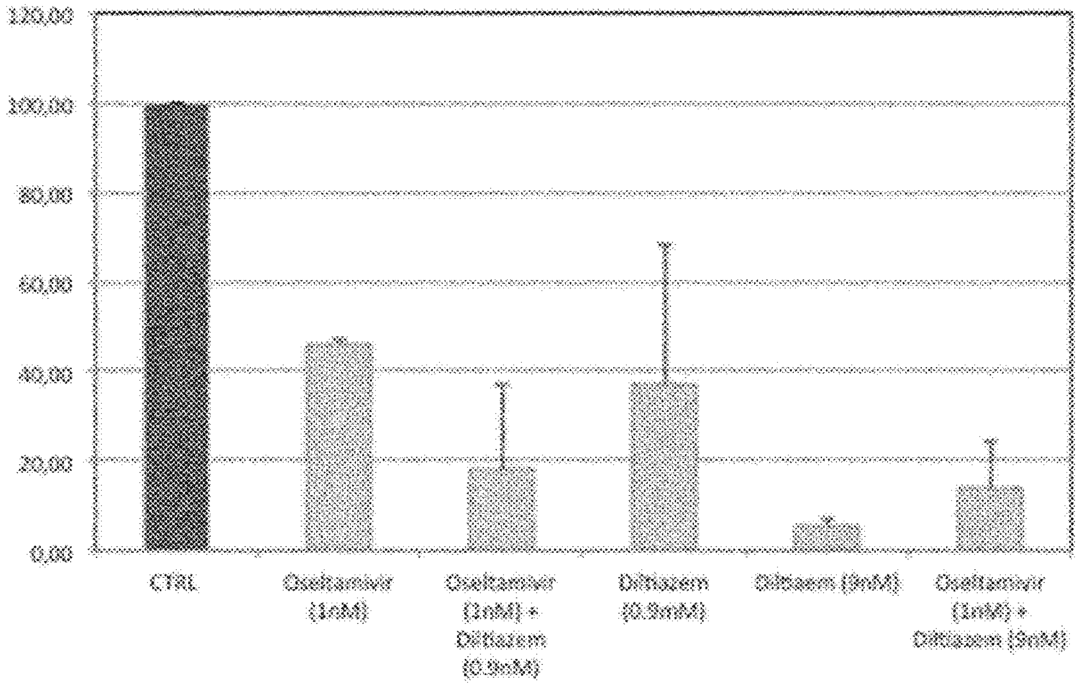

Data for Drug: Dil [nM]

| Dose | Effect |
|---|---|
| 2250.0 | 0.38 |
| 562.5 | 0.38 |
| 140.6 | 0.04 |
| 35.2 | 0.03 |
| 8.8 | 0.02 |

5 data points entered.
X-int: 3.56521
Y-int: -2.5188 +/- 0.39177
m: 0.70649 +/- 0.16954
Dm: 3674.59
r: 0.92341

Data for Drug: OSE [nM]

| Dose | Effect |
|---|---|
| 20.0 | 0.51 |
| 5.0 | 0.37 |
| 1.25 | 0.35 |
| 0.31 | 0.24 |
| 0.08 | 0.11 |

5 data points entered.
X-int: 1.17049
Y-int: -0.4129 +/- 0.05013
m: 0.35277 +/- 0.05866
Dm: 14.8078
r: 0.96094

Data for Drug Combo: D+O (Dil +OSE [2250:20]

| Total Dose | Effect |
|---|---|
| 2270.0 | 0.78 |
| 567.5 | 0.55 |
| 141.85 | 0.44 |
| 35.5129 | 0.32 |
| 8.87822 | 0.13 |

5 data points entered.
X-int: 2.38824
Y-int: -1.2558 +/- 0.12281
m: 0.52584 +/- 0.05306
Dm: 244.479
r: 0.98507

CI Data for Drug Combo: D+O (Dil +OSE [2250:20])

| Fa | CI Value | S.D.A. Analysis |
|---|---|---|
| 0.5 | 0.21141 | 0.21405 +/- 0.05035 |
| 0.55 | 0.19333 | 0.19666 +/- 0.05244 |
| 0.6 | 0.17996 | 0.18426 +/- 0.05494 |
| 0.65 | 0.17075 | 0.17627 +/- 0.05849 |
| 0.7 | 0.16555 | 0.17260 +/- 0.06407 |
| 0.75 | 0.16470 | 0.17374 +/- 0.07307 |
| 0.8 | 0.16931 | 0.18113 +/- 0.08773 |
| 0.85 | 0.18212 | 0.19825 +/- 0.11262 |
| 0.9 | 0.21068 | 0.23485 +/- 0.16044 |
| 0.95 | 0.28537 | 0.33139 +/- 0.28794 |
| 0.97 | 0.36317 | 0.43543 +/- 0.43612 |

| *CI* | Description |
|---|---|
| < 0.1 | Very Strong Synergism |
| 0.1–0.3 | Strong Synergism |
| 0.3–0.7 | Synergism |
| 0.7–0.85 | Moderate Synergism |
| 0.85–0.90 | Slight Synergism |
| 0.90–1.10 | Nearly Additive |
| 1.10–1.20 | Slight Antagonism |
| 1.20–1.45 | Moderate Antagonism |
| 1.45–3.3 | Antagonism |
| 3.3–10 | Strong Antagonism |
| > 10 | Very Strong Antagonism |

ANTIVIRAL COMPOSITIONS FOR TREATING THE FLU

The invention relates to compositions for use in the treatment of viral infections related to flu viruses, in humans and animals.

The viruses responsible for the flu are the influenza viruses, which are divided into three types: A, B and C. Located on the surface of the viruses are two glycoproteins which play an important role in the infection of cells of the infected organism: hemagglutinin (HA) and neuraminidase (NA). There are various influenza A virus subtypes according to the nature of the HA and NA glycoproteins on their surface: 16 types of HA and 9 types of NA have been identified in viruses circulating in the animal world, notably among migratory sea birds. Influenza viruses can thus be defined by the type of protein on their surface.

In humans, the viruses circulating for several decades are subtypes H1N1, H2N2 and H3N2, with occasional interspecies transmission, notably from animal to man, of avian viruses H5N1, H7N7, H7N9, H5N2 and H9N2. As demonstrated by the recent emergence of a new pandemic H1N1 influenza virus of porcine, avian and human origin (porcine, avian and human reassortant virus), influenza A viruses are a serious threat to public health. Flu pandemics are the result notably of antigenic shifts corresponding to the appearance of viruses bearing new surface glycoproteins (HA and NA) in the human population. These shifts allow direct transmission in humans of animal viruses, notably avian viruses, which is the case of epidemics of highly pathogenic avian H5N1 since 2003 in Asia, or of the epidemics of H7N7 influenza in the Netherlands in 2003 and of H7N9 in Southeast Asia in 2013. Antigenic shifts are the result of genetic rearrangement between avian, porcine and human viruses, with pigs playing the intermediate role of host, for example. This genetic rearrangement was notably the source of the H1N1 pandemic in 2009. Furthermore, seasonal flu epidemics, which are notably the result of genetic drift (appearance of mutations in the surface glycoproteins) are a major cause of increased morbidity and mortality, notably in the human population, especially in the very young, the old, the immunosuppressed and those with cardiopulmonary disease.

Vaccination remains the cornerstone of flu prevention. However, when a new virus appears, a period of 6 to 9 months is needed to develop and deliver a new vaccine, and the use of antiviral drugs must be considered for treatment and/or prevention. Common antivirals are M2 channel inhibitors, such as amantadine, and neuraminidase inhibitors, such as zanamivir and oseltamivir.

The use of these drugs is limited by the recurrent appearance of resistance, notably observed for the pandemic H1N1 virus. Moreover, it is not impossible that new emerging viruses are already resistant to these molecules. Finally, most of these molecules cannot be administered systemically, which poses a problem in the event of serious infections.

It thus appears necessary to develop or identify new antiviral compounds which are more effective and which have a broad spectrum of action. A solution for the development of new broad-spectrum therapeutic molecules is to identify molecules having action on the cellular pathways and factors that viruses target to carry out their replication cycle. This strategy, presented in the article by Josset et al. (PLoS One, 2010), made it possible to identify a first series of molecules having unexpected antiviral activity, such as the molecules presented in patent application FR 2 953 410.

In the context of the present invention, several molecules were selected and evaluated in a cellular test of viral infection and in an in vivo murine model. Certain molecules had an antiviral effect not only on an influenza A strain of the H1N1 subtype but also on a strain of the H3N2 subtype. The selected compounds had been described initially as active ingredients in the treatment of pathologies quite different from viral infections. Unexpectedly, it has now been shown that certain of these compounds have antiviral activity, in particular against various subtypes of influenza A virus.

SUMMARY OF THE INVENTION

The invention relates to pharmaceutical or veterinary compositions for use in the prevention and/or treatment of infections with influenza viruses, comprising at least one compound selected from etilefrine and diltiazem.

These pharmaceutical or veterinary compositions may advantageously further comprise at least one other antiviral agent and/or antibacterial agent. These compositions may be in the form of combination products for simultaneous, separate or sequential use in human or veterinary therapy, in particular in the prevention and/or treatment of infections with influenza viruses.

The invention also relates to pharmaceutical or veterinary compositions comprising at least one antiviral agent in combination with at least one compound selected from diltiazem and etilefrine, or a combination of both.

According to a preferred aspect of the invention, these pharmaceutical or veterinary compositions are in a particular dosage form intended for administration by inhalation.

The invention also relates to pharmaceutical or veterinary compositions comprising, in a suitable pharmaceutical carrier, a combination of diltiazem and etilefrine.

FIGURES

FIG. 1A-D, (A) Experimental protocol; In vitro evaluation of the antiviral effect of compounds known for their antiviral activity (1B: ribavirin, monensin) and the compounds lanatoside C (1C) and diltiazem and etilefrine (1D) on A549 cells infected with H1N1 pdm09 virus. The solid line represents normalized virus production (percentage) as a function of the concentration of the compounds (μM). The dotted line represents normalized cell viability (percentage) as a function of the concentration of the compounds (μM).

FIG. 2. In vitro evaluation of the antiviral effect of etilefrine on A549 cells infected with H3N2 virus. The solid line (round points) represents normalized virus production (percentage) as a function of the concentration of etilefrine (μM). The dotted line (square points) represents normalized cell viability (percentage) as a function of the concentration of etilefrine (μM).

FIG. 3A-B. In vitro evaluation of the antiviral effect of etilefrine (A) and diltiazem (B), in combination with oseltamivir, on A549 cells infected with H1N1 pdm09 virus. The graph represents normalized virus production (percentage) for each condition.

FIG. 4. In vivo evaluation of the toxicity of the following molecules: oseltamivir, monensin, diltiazem, etilefrine and isoxicam. The "Saline" control indicates the weight of mice treated with PBS. The curve represents the change in weight (weight gain/loss expressed as a percentage) of the various groups of mice over time.

FIG. 5A-D. In vivo evaluation of the antiviral effect of the compounds oseltamivir, monensin, diltiazem, etilefrine and isoxicam, administered before H1N1 infection of the mice:

(A) Experimental protocol; (B) Survival rate over time, up to 14 days post-infection; (C) Weight loss observed over time; (D) Virus titer measured in the lungs of infected mice at 5 days post-infection.

FIG. 6A-D. In vivo evaluation of the antiviral effect of the compounds oseltamivir and diltiazem, administered 24 hours after H1N1 infection of the mice. Experimental protocol (A); Survival rate over time, after in vivo treatment with PBS alone "Saline" (B), Oseltamivir (C) and Diltiazem (D) administered 24 hours after H1N1 infection of the mice.

FIG. 7A-C. In vitro evaluation of the antiviral effect of diltiazem in combination with other antiviral agents on A549 cells infected with H1N1 pdm09 virus. (A) Post-infection cell treatment protocol; (B) Results obtained for the combination diltiazem and oseltamivir, (C) Results obtained for the combination diltiazem and monensin.

FIG. 8A-E. In vitro evaluation of the antiviral effect of diltiazem in combination with oseltamivir on reconstituted human airway epithelia (HAE) infected with different influenza virus subtypes.

(A) Post-infection HAE treatment protocol;

In all graphs, the black line represents untreated, infected cells.

(B) Results obtained for single-treatment of influenza H1N1 pdm09 with diltiazem (light grey) 9 μM (dotted line) and 90 μm (solid line), or with oseltamivir (dark grey) 0.1 μM (dotted line) and 1 μM (solid line);

(C) Results obtained for the combination diltiazem and oseltamivir at 9/0.1 μM (grey dotted line) and 90/1 μM (grey solid line) in HAE infected with influenza H1N1 pdm09;

(D) Results obtained for the combination diltiazem and oseltamivir at 9/0.1 μM (grey solid line) in HAE infected with influenza H3N2;

(E) Results obtained for the combination diltiazem and oseltamivir at 90/1 μM (grey solid line) in HAE infected with influenza B.

FIG. 9A-C. In vitro evaluation of the antiviral effect and synergistic potential of the diltiazem and oseltamivir combination in A549 cells infected with H1N1, as calculated using the CompuSyn software.

(A) Post-infection A549 cells treatment protocol;

(B) Dose-effect values and key parameters (m: potency, Dm; shape, r: conformity) for the Combination Index (CI) analysis;

(C) Combination Index (CI) values obtained for antiviral activity levels (Fa) between 50% and 97%.

DETAILED DESCRIPTION OF THE INVENTION

The present invention relates to a pharmaceutical or veterinary composition for use in the prevention and/or treatment of infection with influenza viruses, characterized in that it comprises, in a suitable pharmaceutical carrier, at least one compound selected from etilefrine, diltiazem, and derivatives thereof.

These compounds are known for use in other therapeutic applications unrelated to antiviral activity against influenza viruses in humans or animals. It is now demonstrated that these compounds, unexpectedly, have antiviral activity against various subtypes of influenza virus A.

Diltiazem is commonly used to treat angina, high blood pressure, myocardial ischemia, and tachycardia. Diltiazem is a powerful vasodilator.

Several patent applications describe methods for producing diltiazem (EP0728751, EP0561861) and diltiazem derivatives (EP0450705, EP0355395).

This molecule, a member of the benzothiazepine family, has the following chemical structural formula:

Formula (1)

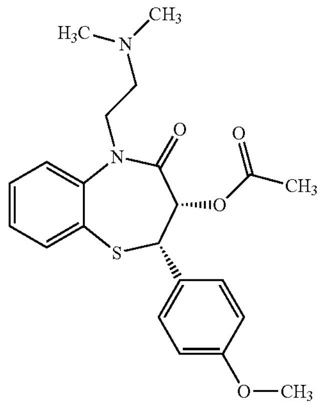

Diltiazem acts by slowing the entry of transmembrane calcium into myocardial muscle fiber and vascular smooth muscle fiber, and thus decreases the intracellular calcium concentration reaching the contractile proteins. Diltiazem thus reduces heart work and slows the ventricular rate.

Patent application WO 87/07508 describes the use of therapeutic compounds that inhibit the influx of calcium into the cell, such as diltiazem, in combination with other antiviral agents for treating viral infections related to cytomegalovirus and to herpes.

Patent application WO 2011/126071 describes the use of therapeutic compounds that inhibit the influx of calcium into the cell, such as diltiazem, for treating viral infections, notably those related to influenza viruses. More specifically, that application indicates that diltiazem can inhibit the interaction between a virus and calcium channels, and thus block the entry of the virus into cells.

On the contrary, in the present invention, it is shown that diltiazem acts in an overall manner on target cells by strongly modulating gene expression in these cells, and by thus inducing an overall cellular state unfavorable to viral infection. Indeed, and as presented in further detail in the introduction to the examples, the selected molecules are associated with cellular gene expression profiles that are the opposite of those characteristic of an infectious state. Moreover, WO 2011/126071 proposes a diltiazem concentration more than 100 times higher than the concentrations proposed in the present application.

The amounts of diltiazem conventionally used in humans are preferably between 200 and 300 mg/day, for a typical dosing regimen, when the diltiazem is in tablet form.

Diltiazem is available in various dosage forms, such as powder for injectable solution (CN102657621) or pharmaceutical preparations for inhalation (WO 02/094238, U.S. Pat. No. 4,605,552).

In the context of the present invention, the term "diltiazem" means diltiazem in all its forms, notably in the form of salts, and the term "diltiazem derivative" means all the molecules derived from the formula (1) presented above, having the same biological activity, notably the same antiviral activity, said antiviral activity being obtained by inducing an overall cellular state unfavorable to viral infection, by acting on the expression of a certain number of genes of target cells.

Etilefrine has been described as a cardiac stimulant, and is commonly used as an anti-hypotensive agent, notably in the treatment of neurological and cardiovascular orthostatic hypotension of the endocrine system or of metabolic origin. Its use was notably described in patent application EP0162320.

Etilefrine increases cardiac output, stroke volume and venous return and raises central venous pressure and arterial pressure, via a direct sympathomimetic effect on alpha-1 and beta-adrenergic receptors, by its positive inotropic action. Moreover, it increases venous tone and leads to an increase in circulating blood volume.

It is a sympathomimetic amine of the 3-hydroxy-phenylethanolamine series having the chemical structural formula:

Formula (2)

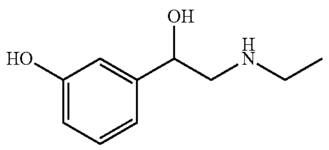

The amounts conventionally used in humans are preferably about 30 mg/day, generally administered in three doses.

Etilefrine is available in various dosage forms, such as in the form of injectable liquid solutions, oral liquid solutions, and tablets.

Modes of administration by inhalation have also been described for other beta-adrenergic receptor agonists.

In the context of the present invention, the term "etilefrine" means etilefrine in all its forms, notably in the form of salts, and the term "etilefrine derivatives" means all the molecules derived from the formula (2) presented above, having the same biological activity, notably the same antiviral activity, said antiviral activity being obtained by inducing an overall cellular state unfavorable to viral infection, by acting on the expression of a certain number of genes of target cells.

According to the invention, influenza viruses are type A viruses having humans or animals as host. The terms "flu virus" and "influenza virus" are used interchangeably in the application and denote the same viruses.

The expression "infection with influenza viruses" should be understood as being infection generated by the presence of at least one known influenza virus, said virus having infected the individual or the animal, or being capable of infecting the individual or the animal, to which the composition is administered.

According to the invention, the term "suitable pharmaceutical carrier" denotes pharmaceutically acceptable carriers or excipients according to the invention, i.e., carriers or excipients whose administration to an individual or an animal is not accompanied by significant deleterious effects, and which are well-known to a person skilled in the art.

In particular, the compositions of the present invention are used for the prevention and/or treatment of infections with influenza A viruses. Advantageously, the compositions of the present invention have a broad spectrum of action against the various subtypes of influenza A viruses.

In an embodiment, the compositions of the present invention are used for the prevention and treatment of infections with type A viruses circulating mainly in humans and animals.

There are various subtypes of influenza A virus according to the nature of the HA and NA glycoproteins on their surface. According to a particular aspect, the flu virus is a type A virus selected from the H1N1, H2N2, H3N2, H5N1, H7N7, H7N9, H5N2 and H9N2 subtypes.

In another embodiment, the influenza virus is a type B virus.

The invention thus relates to the prevention and/or treatment of infections with flu viruses in humans, i.e., to a pharmaceutical composition for use in the prevention and/or treatment of infection with influenza viruses.

The invention also relates to the prevention and/or treatment of infections with flu viruses in animals, in particular in livestock such as pigs, horses and poultry. More particularly, the invention relates to the prevention and/or treatment of infections with influenza viruses in poultry, and more particularly in hens, ducks, geese and turkeys. The invention also relates to the prevention and treatment of infections with flu viruses in other animals such as, for example, horses, cats, dogs and felids. According to this aspect, the invention thus relates to a veterinary composition for use in the prevention and/or treatment of infection with influenza viruses.

The compositions according to the invention are in particular intended for use in the prevention of infection with influenza viruses.

The term "prevention" refers to the fact of preventing, or at least decreasing, the probability of the appearance of an infection in a human or animal organism by at least one influenza virus. By administering at least one composition according to the invention, the human or animal cells of said organism become more resistant and are less likely to be infected with said virus.

The compositions according to the invention may also be intended for use in the treatment of infection with influenza viruses.

The term "treatment" refers to the fact of fighting infection with at least one influenza virus in a human or animal organism. By administering at least one composition according to the invention, the level of viral infection in the organism will gradually decrease and then completely disappear. The term "treatment" also refers to the fact of alleviating the symptoms associated with viral infection (fever, fatigue, etc.).

According to a first aspect of the invention, the pharmaceutical or veterinary composition comprises an effective amount of diltiazem or a derivative thereof, for use in the prevention and/or treatment of infection with influenza viruses.

According to a second aspect of the invention, the pharmaceutical or veterinary composition comprises an effective amount of etilefrine or a derivative thereof, for use in the prevention and/or treatment of infection with influenza viruses.

According to a third aspect of the invention, the pharmaceutical or veterinary composition comprises a combination of diltiazem and etilefrine or derivatives thereof, for use in the prevention and/or treatment of infection with one or more flu viruses.

This combination comprises either the same amount of each compound (composition at 50/50 by weight) or unequal amounts of each compound, such as 90% diltiazem and 10% etilefrine, 80% diltiazem and 20% etilefrine, 70% diltiazem and 30% etilefrine, 60% diltiazem and 40% etilefrine, 40% diltiazem and 60% etilefrine, 30% diltiazem and 70% etilefrine, 20% diltiazem and 80% etilefrine, or even 10% diltiazem and 90% etilefrine.

According to a particular aspect of the invention, the pharmaceutical or veterinary composition for use as described above is characterized in that it further comprises another antiviral agent.

Indeed, diltiazem and etilefrine or mixtures thereof can be employed in therapy alone or in combination with at least one other active agent. These may be compounds for enhancing the activity of the compounds, or other active agents known for use as antiviral agents in the treatment of infection with influenza viruses.

In particular, the antiviral agent has a direct inhibitory activity on influenza viruses, i.e., inhibits the replication or prevents the penetration or the propagation of at least one influenza virus in an infected organism.

Such active agents are well-known to a person skilled in the art and available commercialy or are described in reference works such as the drug database published by Vidal (Le Dictionnaire Vidal).

According to a first aspect of the invention, the pharmaceutical or veterinary composition comprises diltiazem and an antiviral agent, for use in the prevention and/or treatment of infection with influenza viruses.

According to a second aspect of the invention, the pharmaceutical or veterinary composition comprises etilefrine and an antiviral agent, for use in the prevention and/or treatment of infection with influenza viruses.

According to a third aspect of the invention, the pharmaceutical or veterinary composition comprises a combination of diltiazem and etilefrine, and an antiviral agent, for use in the prevention and/or treatment of infection with influenza viruses.

In particular, this antiviral agent is selected from viral agents having a direct inhibitory action on the viruses, such as oseltamivir (also called Tamiflu), zanamivir, peramivir, amantadine, rimantadine, ribavirin and arbidol.

This antiviral agent may also be selected from agents active on the cells, inducing overall cellular states unfavorable to viral infection, such as monensin, midodrine, desglymidodrine, rilmenidine, harmol, harmol dimers, and brinzolamide.

According to a preferred aspect of the invention, this antiviral agent is monensin, a molecule having calcium chelating activity in the extracellular medium.

This antiviral agent may also be selected from:

viral polymerase inhibitors (e.g., T705);

nucleoprotein inhibitors;

hemagglutinin inhibitors;

neuraminidase inhibitors;

NS1, M1, M2, Pb1-F2, NEP protein inhibitors;

This antiviral agent may also be selected from:

recombinant sialidases (e.g., DAS181);

NFKB inhibitors;

HSP90 inhibitors; and

Inhibitors of the cellular protein kinase Mek, Erk or PKC.

It is understood that this antiviral agent will be used in the amounts necessary to have antiviral action, this amount being designated as being "effective", this proportion being easily determined by a person skilled in the art.

According to another preferred aspect of the invention, the pharmaceutical or veterinary composition comprises diltiazem, in combination with oseltamivir, for use in the prevention and/or treatment of infection with influenza viruses. Advantageously, this combination of diltiazem and oseltamivir presents significant effects against several strains of influenza virus (FIGS. 8A to 8E). Furthermore, a synergy of effects is demonstrated (FIGS. 9A to 9C, and table 1).

According to a particular aspect, the pharmaceutical or veterinary composition comprises diltiazem, in combination with zanamivir, for use in the prevention and/or treatment of infection with influenza viruses.

According to a particular aspect, the pharmaceutical or veterinary composition comprises diltiazem, in combination with peramivir, for use in the prevention and/or treatment of infection with influenza viruses.

According to a particular aspect, the pharmaceutical or veterinary composition comprises diltiazem, in combination with amantadine, for use in the prevention and/or treatment of infection with influenza viruses.

According to a particular aspect, the pharmaceutical or veterinary composition comprises diltiazem, in combination with rimantadine, for use in the prevention and/or treatment of infection with influenza viruses.

According to a particular aspect, the pharmaceutical or veterinary composition comprises diltiazem, in combination with ribavirin, for use in the prevention and/or treatment of infection with influenza viruses.

According to a particular aspect, the pharmaceutical or veterinary composition comprises diltiazem, in combination with arbidol, for use in the prevention and/or treatment of infection with influenza viruses.

According to another aspect of the invention, the pharmaceutical or veterinary composition comprises diltiazem and monensin, for use in the prevention and/or treatment of infection with influenza viruses.

According to another aspect of the invention, the pharmaceutical or veterinary composition comprises diltiazem, monensin and oseltamivir, for use in the prevention and/or treatment of infection with influenza viruses.

According to another aspect of the invention, the pharmaceutical or veterinary composition comprises diltiazem, monensin and zanamivir, for use in the prevention and/or treatment of infection with influenza viruses.

According to another aspect of the invention, the pharmaceutical or veterinary composition comprises diltiazem, monensin and peramivir, for use in the prevention and/or treatment of infection with influenza viruses.

According to another aspect of the invention, the pharmaceutical or veterinary composition comprises diltiazem, monensin and amantadine, for use in the prevention and/or treatment of infection with influenza viruses.

According to another aspect of the invention, the pharmaceutical or veterinary composition comprises diltiazem, monensin and rimantadine, for use in the prevention and/or treatment of infection with influenza viruses.

According to another aspect of the invention, the pharmaceutical or veterinary composition comprises diltiazem, monensin and ribavirin, for use in the prevention and/or treatment of infection with influenza viruses.

According to another aspect of the invention, the pharmaceutical or veterinary composition comprises diltiazem, monensin and arbidol, for use in the prevention and/or treatment of infection with influenza viruses.

According to a second preferred aspect of the invention, the pharmaceutical or veterinary composition comprises etilefrine, in combination with oseltamivir, for use in the prevention and/or treatment of infection with influenza viruses.

According to a particular aspect, the pharmaceutical or veterinary composition comprises etilefrine, in combination with zanamivir, for use in the prevention and/or treatment of infection with influenza viruses.

According to a particular aspect, the pharmaceutical or veterinary composition comprises etilefrine, in combination with peramivir, for use in the prevention and/or treatment of infection with influenza viruses.

According to a particular aspect, the pharmaceutical or veterinary composition comprises etilefrine, in combination with amantadine, for use in the prevention and/or treatment of infection with influenza viruses.

According to a particular aspect, the pharmaceutical or veterinary composition comprises etilefrine, in combination with rimantadine, for use in the prevention and/or treatment of infection with influenza viruses.

According to a particular aspect, the pharmaceutical or veterinary composition comprises etilefrine, in combination with ribavirin, for use in the prevention and/or treatment of infection with influenza viruses.

According to a particular aspect, the pharmaceutical or veterinary composition comprises etilefrine, in combination with arbidol, for use in the prevention and/or treatment of infection with influenza viruses.

According to another aspect of the invention, the pharmaceutical or veterinary composition comprises etilefrine and monensin, for use in the prevention and/or treatment of infection with influenza viruses.

According to a third preferred aspect of the invention, the pharmaceutical or veterinary composition comprises a combination of diltiazem and etilefrine, in combination with oseltamivir, for use in the prevention and/or treatment of infection with influenza viruses.

The pharmaceutical or veterinary composition for use according to the invention may also comprise at least one antibacterial agent. Such an agent will be in particular an antibiotic, intended to prevent the bacterial superinfections classically observed in complications of infections with influenza viruses.

According to a first aspect of the invention, the pharmaceutical or veterinary composition comprises diltiazem, in combination with at least one antibacterial agent, for use in the prevention and/or treatment of infection with influenza viruses.

According to a second aspect of the invention, the pharmaceutical or veterinary composition comprises etilefrine, in combination with at least one antibacterial agent, for use in the prevention and/or treatment of infection with influenza viruses.

According to a third aspect of the invention, the pharmaceutical or veterinary composition comprises a combination of diltiazem and etilefrine, in combination with at least one antibacterial agent, for use in the prevention and/or treatment of infection with influenza viruses.

According to a fourth aspect of the invention, the pharmaceutical or veterinary composition comprises a combination of diltiazem and etilefrine, in combination with an antiviral agent, notably oseltamivir, and at least one antibacterial agent, for use in the prevention and/or treatment of infection with influenza viruses.

According to a fifth aspect of the invention, the pharmaceutical or veterinary composition comprises a combination of diltiazem and monensin, in combination with an antiviral agent, such as one of the combinations mentioned above, and at least one antibacterial agent, for use in the prevention and/or treatment of infection with influenza viruses.

Combination Product

The present invention also relates to a combination product comprising at least one compound selected from etilefrine and diltiazem, and at least one antiviral agent and/or antibacterial agent, for simultaneous, separate or sequential use, for preventing and/or treating infection with influenza viruses, in humans or animals.

According to an embodiment, said combination product comprises diltiazem and at least one antiviral agent such as oseltamivir or monensin.

According to another embodiment, said combination product comprises etilefrine and at least one antiviral agent such as oseltamivir or monensin.

According to another embodiment, said combination product comprises a combination of diltiazem and etilefrine and at least one antiviral agent such as oseltamivir or monensin.

According to another embodiment, said combination product comprises diltiazem and at least one antibacterial agent.

According to another embodiment, said combination product comprises etilefrine and at least one antibacterial agent.

According to another embodiment, said combination product comprises a combination of diltiazem and etilefrine and at least one antibacterial agent.

According to another embodiment, said combination product comprises diltiazem, at least one antiviral agent, and at least one antibacterial agent.

According to another embodiment, said combination product comprises etilefrine, at least one antiviral agent, and at least one antibacterial agent.

According to another embodiment, said combination product comprises a combination of diltiazem and etilefrine, at least one antiviral agent, and at least one antibacterial agent.

Antiviral agents, notably having an inhibitory action against influenza viruses, are well-known to a person skilled in the art, and will notably be selected from the following agents:

- oseltamivir, zanamivir, peramivir, amantadine, rimantadine, ribavirin and arbidol;
- midodrine, desglymidodrine, rilmenidine, harmol, harmol dimers, brinzolamide and monensin;
- viral polymerase inhibitors (e.g., T705);
- nucleoprotein inhibitors;
- hemagglutinin inhibitors;
- neuraminidase inhibitors;
- NS1, M1, M2, NEP, Pb1-F2 protein inhibitors;
- recombinant sialidases (e.g., DAS181);
- NFKB inhibitors;
- HSP90 inhibitors; and
- Inhibitors of the cellular protein kinase Mek, Erk or PKC.

The invention also relates to a combination product comprising at least one compound selected from etilefrine and diltiazem, and at least one other antiviral agent and/or antibacterial agent, for simultaneous, separate or sequential use, for preventing and/or treating infections with influenza viruses.

In particular, the present invention relates to a combination product comprising diltiazem and oseltamivir, for simultaneous, separate or sequential use, for preventing and/or treating infections with influenza viruses.

The invention also relates to a therapeutic method for preventing and/or treating infection with influenza viruses (flu viruses) in humans, wherein a patient is administered an effective amount of a compound selected from etilefrine and diltiazem, or a mixture of both, optionally in combination with another antiviral compound and/or an antibacterial compound.

In particular, the present invention relates to a therapeutic method for preventing and/or treating infection with influenza viruses (flu viruses) in humans, wherein a patient is administered an effective amount of diltiazem in combination with oseltamivir, optionally with an antibacterial compound.

The invention also relates to a therapeutic method for preventing and/or treating infection with influenza viruses in animals, wherein an animal is administered an effective amount of a compound selected from etilefrine and diltiazem, optionally in combination with another antiviral compound and/or an antibacterial compound. Advantageously, the animal is a farm animal such as, for example, a pig, a horse or even a hen or a pet (dog, cat, etc.).

In particular, the present invention relates to a veterinary method for preventing and/or treating infection with influenza viruses (flu viruses) in animals, wherein an animal is administered an effective amount of diltiazem in combination with oseltamivir, optionally with an antibacterial compound.

Formulation of the Pharmaceutical or Veterinary Compositions

According to a preferred aspect of the invention, the pharmaceutical or veterinary composition for use in the prevention and/or treatment of infection with influenza viruses is characterized in that it is in a dosage form intended for administration by inhalation.

The term "inhalation" denotes absorption by the respiratory tract. It is in particular a method of absorption of therapeutic compounds of certain substances in the form of gas, microdroplets, or powder in suspension.

The administration of pharmaceutical or veterinary compositions by inhalation, i.e., by the nasal and/or oral routes, is well-known to a person skilled in the art.

Two types of administration by inhalation can be distinguished:

- administration by insufflation when the compositions are in powder form, and
- administration by nebulization when the compositions are in aerosol (suspension) form or in the form of pressurized solutions, for example aqueous solutions. In this case, the use of a nebulizer or a sprayer will be recommended to administer the pharmaceutical or veterinary composition.

The dosage form considered here is thus selected from a powder, an aqueous suspension of droplets, or a pressurized solution.

Pharmaceutical or Veterinary Compositions

The present invention also relates to a pharmaceutical or veterinary composition comprising, in a suitable pharmaceutical carrier, at least one antiviral agent in combination with at least one compound selected from etilefrine and diltiazem, or a combination of both.

According to a preferred aspect, the antiviral agent is selected from the antiviral agents well-known to a person skilled in the art, and conventionally used to prevent or treat the flu, notably having a direct inhibitory action against influenza viruses, i.e., inhibiting the replication or preventing the penetration or the propagation of at least one influenza virus in an infected organism.

The antiviral agent is notably selected from oseltamivir, zanamivir, peramivir, amantadine, rimantadine, ribavirin and arbidol.

This antiviral agent may also be selected from agents active on the cells, inducing overall cellular states unfavorable to viral infection, such as midodrine, desglymidodrine, rilmenidine, harmol, harmol dimers, brinzolamide, and monensin.

This antiviral agent may also be selected from:

- viral polymerase inhibitors (e.g., T705);
- nucleoprotein inhibitors;
- hemagglutinin inhibitors;
- neuraminidase inhibitors;
- NS1, M1, M2, NEP, Pb1-F2 protein inhibitors;

This antiviral agent may also be selected from:

- recombinant sialidases (e.g., DAS181);
- NFKB inhibitors;
- HSP90 inhibitors; and
- Inhibitors of the cellular protein kinase Mek, Erk or PKC.

According to a preferred aspect, the antiviral agent is oseltamivir. According to another preferred aspect, the antiviral agent is monensin.

The invention thus specifically relates to:

- a pharmaceutical or veterinary composition comprising, in a suitable pharmaceutical carrier, at least one antiviral agent with diltiazem; and
- a pharmaceutical or veterinary composition comprising, in a suitable pharmaceutical carrier, at least one antiviral agent with etilefrine; and
- a pharmaceutical or veterinary composition comprising, in a suitable pharmaceutical carrier, at least one antiviral agent with etilefrine and diltiazem.

This antiviral agent will preferably be selected from those listed in the present application, and will be notably oseltamivir or monensin.

It is understood that all the combinations of two, three or four active compounds mentioned above are pharmaceutical or veterinary compositions according to the invention.

According to yet another aspect, the pharmaceutical or veterinary composition according to the invention comprises, in a suitable pharmaceutical carrier, a combination of diltiazem and etilefrine.

As indicated above, any combination of diltiazem and etilefrine comprises either the same amount of each compound (composition at 50/50 by weight) or unequal amounts of each compound, such as 90% diltiazem and 10% etilefrine, 80% diltiazem and 20% etilefrine, 70% diltiazem and 30% etilefrine, 60% diltiazem and 40% etilefrine, 40% diltiazem and 60% etilefrine, 30% diltiazem and 70% etilefrine, 20% diltiazem and 80% etilefrine, or even 10% diltiazem and 90% etilefrine.

It is understood that, in the present description, all the compounds mentioned are present in the pharmaceutical or veterinary compositions in effective amounts, i.e., in amounts that produce the expected antiviral effect. The effective amounts can easily be determined by a person skilled in the art.

The pharmaceutical or veterinary compositions of the present invention are suitable for oral, sublingual, subcutaneous, intramuscular, intravenous, transdermal, ocular, local or rectal administration, wherein the active compound may be administered in single-unit dosage forms, mixed with conventional pharmaceutical excipients, to animals or humans.

Suitable single-unit dosage forms include oral forms such as tablets, gelatin capsules, powders, granules, and oral solutions or suspensions; sublingual and buccal dosage forms; subcutaneous, intramuscular, intravenous, intranasal or intraocular dosage forms; and rectal dosage forms.

When a solid composition is prepared in tablet form, the main active compound is mixed with a suitable pharmaceutical carrier such as gelatin, starch, lactose, magnesium stearate, talc, gum arabic or the like. The tablets can be coated with sucrose or other suitable substances, or else they can be treated so as to have a sustained or delayed activity and to continuously release a predetermined amount of active ingredient.

A preparation in gelatin capsules is obtained by mixing the active compound with a diluent and pouring the resulting mixture into soft or hard gelatin capsules.

A preparation in syrup or elixir form may contain the active compound together with a sweetener, an antiseptic, as well as a flavoring agent and a suitable colorant.

Water-dispersible powders or granules may contain the active compound in mixture with dispersion or wetting agents, or suspension agents, as well as with flavor correctors or sweeteners.

According to a preferred aspect of the invention, the pharmaceutical or veterinary composition is in a dosage form intended for local administration, such as administration via the mucous membranes of the respiratory tract, i.e., administration by inhalation.

EXAMPLES

Introduction

Studies of the cellular transcriptomic response during influenza infection revealed the signaling pathways called upon and/or diverted during infection, in vitro in cells in culture. That made it possible to characterize specific in vitro "transcriptomic signatures" of infection with various human and avian influenza viruses (Josset et al. PLoS One, 2010; Terrier et al. Virol J, 2011; Terrier et al. J Gen Virol, 2013).

This same strategy was applied to cell samples in vivo, derived from nasal washings of 9 patients, in order to characterize the in vivo signatures of infection with pandemic H1N1 virus (pdm09). These transcriptomic signatures were obtained on the Affymetrix Fluidics Station 450, by means of various bioinformatics analysis tools. After "in silico" screening in public databases such as Connectivity Map (Broad Institute, MIT), 34 molecules were selected, including, inter alia, etilefrine, diltiazem, monensin, lanatoside C, and isoxicam. These molecules were evaluated for their antiviral activity in an in vitro infection cell model, on the A549 human lung epithelial cell line, then in vivo in an infectious murine model.

Example 1. In vitro evaluation of the antiviral effect of various selected compounds on A549 cells infected with H1N1.

Detailed Culture and Infection Protocol:

A. Culture of Human A549 Cells

A549 (lung carcinoma) cells are maintained in Dulbecco's Modified Eagle Medium (DMEM, BioWhittaker) supplemented with 10% (v/v) fetal calf serum, 2 mM L-glutamine, 100 U/mL penicillin and 100 μg/mL streptomycin, in an incubator at 37° C., in an atmosphere saturated with moisture containing 5% $CO_2$. At confluence, the cells are detached from the support by treatment with trypsin-EDTA and are re-seeded in a culture flask containing 15 mL of fresh medium. Three days before the infection step, $0.75 \cdot 10^6$ cells are distributed in 25 $cm^2$ (T25) flasks in medium with 10% fetal calf serum in such a way as to obtain 70-80% confluence during infection.

B. Infection of Cells by Representative Influenza Viruses

The cells are infected with the various influenza viruses with a multiplicity of infection (MOI) of 0.1 in DMEM, 2 mM L-glutamine, 100 U/mL penicillin, 100 μg/mL streptomycin, and 0.5 μg/mL trypsin.

The viruses used are the H1N1 (A/Pdm/09) and H3N2 (A/Moscow/10/99) strains of human influenza A virus.

C. Pretreatment and Treatment

The molecules were tested on A549 cells at 70-80% confluence. The cells were incubated for 6 h with various concentrations of molecules, then were infected with the various viruses for 1 h, and were returned to the presence of the molecules, at the same concentrations.

D. Measurements

A cytotoxicity test and a virus quantification test are performed after 48 h of incubation at 37° C. under 5% $CO_2$. The cytotoxicity of the various molecules is determined in each test in a plate of uninfected cells by a viability test (MTS assay, Promega). This test is based on measuring the metabolic activity of the cells, which transforms a substrate (MTS tetrazolium) into a product (formazan) that is soluble in the medium and whose absorbance measured at 490 nm is a proportional reflection of the number of living cells. The ratio of the absorbance in each well to the mean absorbance of the wells containing control cells (not treated with the molecules) is calculated and shown on the diagrams as an indication of cell viability (relative cell viability).

The effect on virus production is estimated by determination of infectious titers ($TCID_{50}$/mL, 50% infectious dose) carried out in MDCK cells, the titers being calculated according to the technique of Reed and Muench. The ratio of the infectious titer in each condition was expressed as a function of the infectious titer measured in the control condition E. Results The cell pretreatment and treatment protocol is shown diagrammatically in FIG. 1A. Several concentrations were tested. The cells are pretreated for 6 hours with the various molecules tested and then subjected to infection with H1N1 pdm09 virus, for 1 hour. Treatment with the various molecules tested is then repeated for 48 hours. The measurements taken at the end of the treatment, as described above, make it possible to determine the median inhibitory concentration ($IC_{50}$), dependent on virus production as a function of the various concentrations tested.

FIG. 1B shows the results obtained for the following molecules: ribavirin, monensin, lanatoside C, diltiazem and etilefrine. As expected, the compounds known for their antiviral activity—ribavirin and monensin—induce a significant decrease in normalized virus production. More surprisingly, diltiazem and etilefrine also cause a significant decrease in normalized virus production. Among the selected compounds as described in the introduction, lanatoside C was tested to evaluate its antiviral activity—the results obtained did not make it possible to confirm the antiviral activity of this compound.

Example 2. In vitro evaluation of the antiviral effect of etilefrine on A549 cells infected with virus subtype H3N2.

The pretreatment and treatment protocol is shown diagrammatically in FIG. 1A, and the experimental conditions are the same as those described in Example 1. The H3N2 virus used for the infection is the A/Moscow/10/99 (H3N2) strain.

FIG. 2 shows that the antiviral effects of etilefrine are significant from the lowest concentration tested and make it possible to completely inhibit virus production with 0.018 μM etilefrine.

Example 3. In vitro evaluation of the antiviral effect of (A) etilefrine and (B) diltiazem, in combination with oseltamivir, on A549 cells infected with H1N1 pdm09 virus.

The pretreatment and treatment protocol is shown diagrammatically in FIG. 1A, and the experimental conditions are the same as those described in Example 1.

As expected, oseltamivir significantly decreases virus production to about 40% (FIGS. 3A and 3B). The combinations of etilefrine and oseltamivir perform much better than the compounds alone, at both etilefrine concentrations tested.

The 0.9 nM combination of oseltamivir and diltiazem is more effective than the compounds alone. The best results are obtained with diltiazem alone at a concentration of 9 nM.

Example 4. In vivo evaluation in mice of the toxicity of the following molecules: oseltamivir, monensin, diltiazem, etilefrine and isoxicam.

The "Saline" control denotes untreated mice, having been treated with PBS.

The following daily amounts were administered by gavage to the mice:

oseltamivir: 10 mg/kg/day etilefrine: 3 mg/kg/day diltiazem: 90 mg/kg/day

The compound having the highest cell toxicity is oseltamivir, this toxicity being acceptable nevertheless, the mice maintaining a weight increase during treatment. Diltiazem (diamonds) and etilefrine (stars) are clearly nontoxic at the administered doses.

Example 5. In vivo evaluation of the antiviral effect of the compounds oseltamivir, monensin, diltiazem, etilefrine and isoxicam on infected B57BL/6 mice: (A) Administration protocol; (B) Survival rate over time, up to 14 days post-infection; (C) Weight loss observed over time; (D) Virus titer in the lungs.

B57BL/6 mice (age 7-8 weeks) are treated by gavage before (Day-1), the day of, and 3 days following infection with H1N1 pdm09 virus, according to the protocol shown diagrammatically in FIG. 5A.

The following parameters are evaluated over time:

FIG. 5B: Survival rate over time, up to 14 days post-infection;

FIG. 5C: Weight loss and gain observed over time;

FIG. 5D: Viral titer in the lungs of infected and treated mice.

Etilefrine (represented by stars) and diltiazem (represented by diamonds) allow maximum survival of the infected mice—i.e., 70% and 90% survival at 14 days, respectively—which is a better result than that obtained for oseltamivir (60% survival; represented by circles).

Example 6. In vivo evaluation of the antiviral effect of the compounds oseltamivir and diltiazem administered 24 hours after infection of the mice with H1N1 pdm09 virus: survival rate over time, up to 14 days post-infection.

B57BL/6 mice (age 7-8 weeks) are treated by gavage after infection with H1N1 pdm09 virus, according to the protocol shown diagrammatically in FIG. 6A. Survival rate over time is measured for infected mice receiving no treatment (FIG. 6B); treated with oseltamivir (FIG. 6C); and treated with diltiazem (FIG. 6D). The survival rate of mice treated with oseltamivir, and of those treated with diltiazem, is 100%.

Example 7. In vitro evaluation of the antiviral effect of diltiazem in combination with oseltamivir on A549 cells infected with H1N1 pdm09 virus (FIG. 7).

The post-infection cell treatment protocol is shown diagrammatically in FIG. 7A. The cells are subjected to infection with H1N1 pdm09 virus for 1 hour and then are treated starting at 6 h post-infection for 48 hours, or are not treated (control measurement: Ctrl). The measurements taken at the end of the treatment, as described above, make it possible to determine the effect of the treatments on virus production.

FIGS. 7B and 7C show the results obtained for the combinations diltiazem and oseltamivir, and diltiazem and monensin, respectively.

In post-infection treatment conditions, oseltamivir (10 nM) significantly decreases virus production to a decreased value of about 55% relative to the control value, and diltiazem (9 μM) significantly decreases the relative viral titer by about 20% relative the control value.

The combination of diltiazem and oseltamivir performs much better than the compounds alone, since it significantly decreases virus production by 70% relative to the control value. Thus, the effects of oseltamivir are potentiated by the presence of diltiazem.

In post-infection treatment conditions, monensin (6 μM) is extremely effective since it significantly decreases virus production by about 72% relative to the control value. As indicated above, diltiazem (9 μM) decreases virus production by about 20%.

The combination of diltiazem and monensin is more effective than the compounds alone, since it significantly decreases virus production by about 82% relative to the control value. Thus, the effects of monensin are potentiated by the presence of diltiazem.

Example 8. In vitro evaluation of the antiviral effect of diltiazem in combination with oseltamivir on reconstituted human airway epithelia (HAE) infected with different influenza virus subtypes (FIG. 8).

The post-infection HAE treatment protocol is shown diagrammatically in FIG. 8A. HAE were infected with the viral strain specified in each case (H1N1 pdm09, H3N2, or B) for 1 hour and treatments on the basolateral medium were initiated 5 h post-infection and continued once daily for 5 consecutive days. The measurements taken at each time-point and at the end of the treatment, make it possible to determine the effect of the treatments on virus production.

Figure 1A:
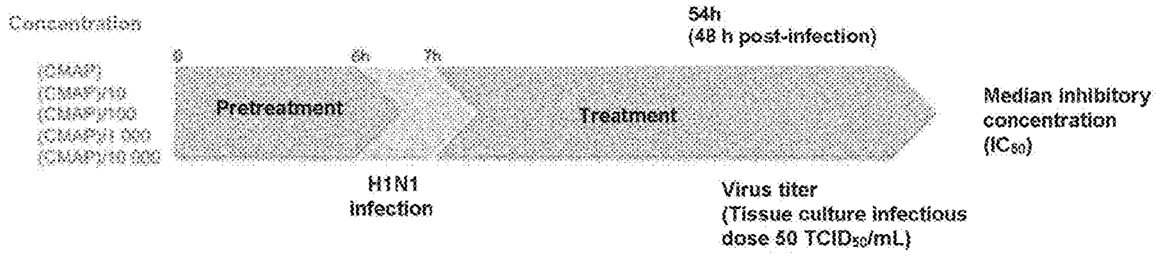
Figure 1B:
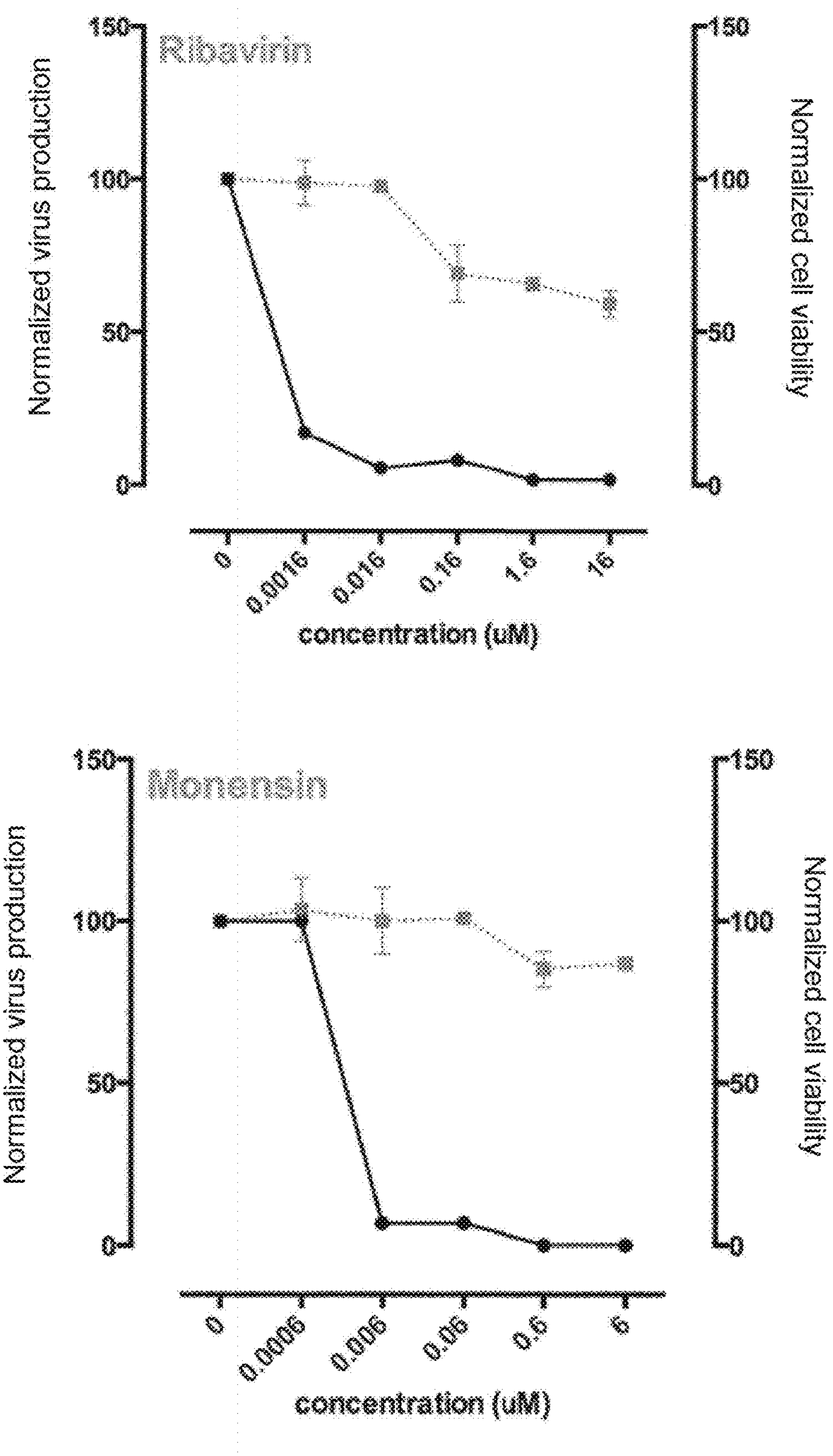
Figure 1C:
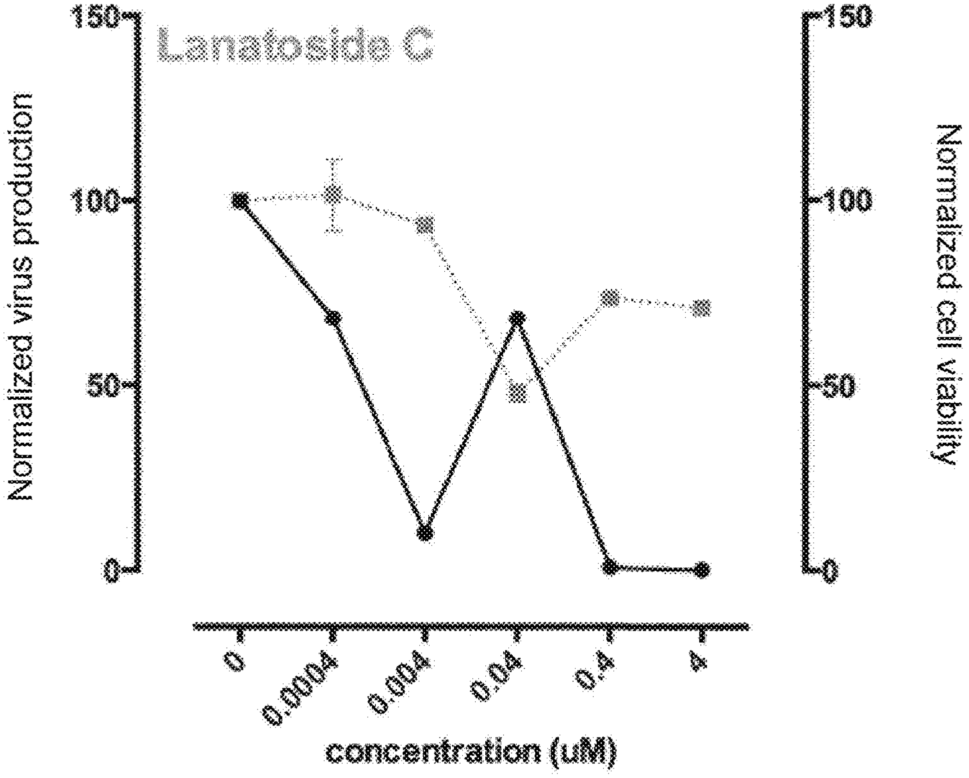
Figure 1D:
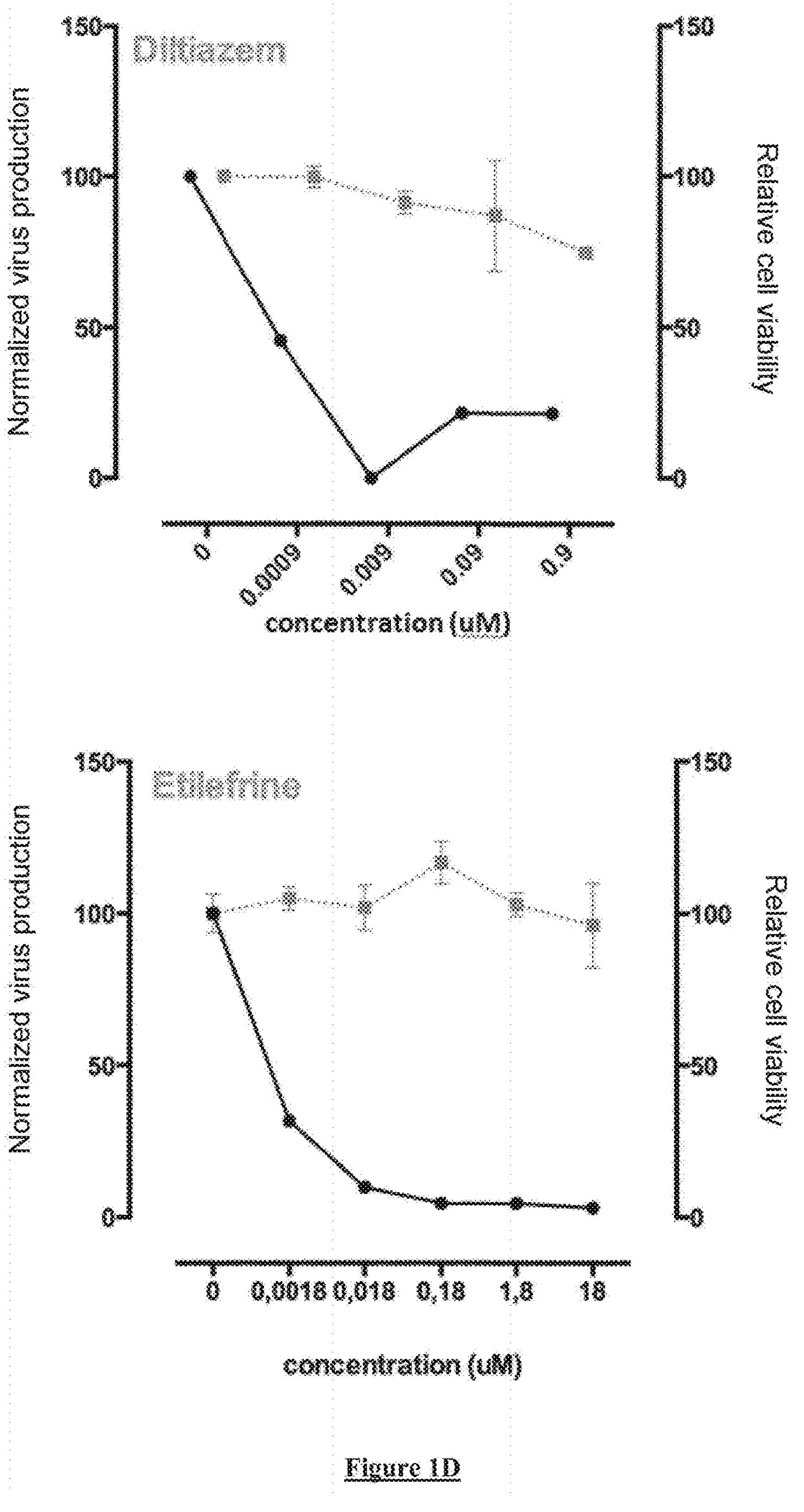
Figure 2:
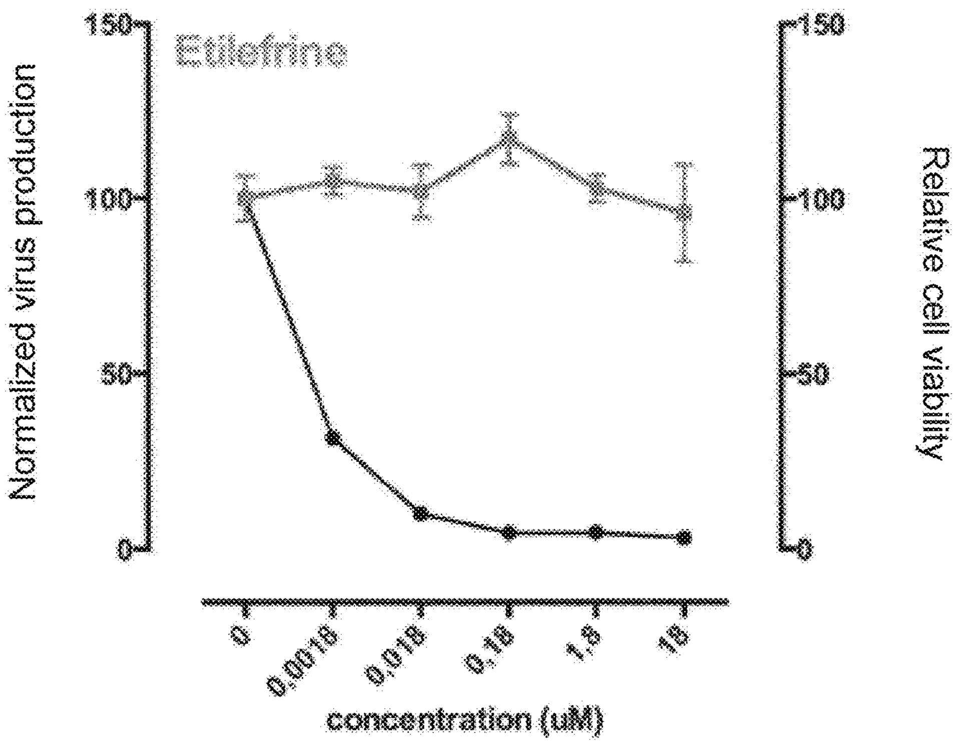
Figure 4:
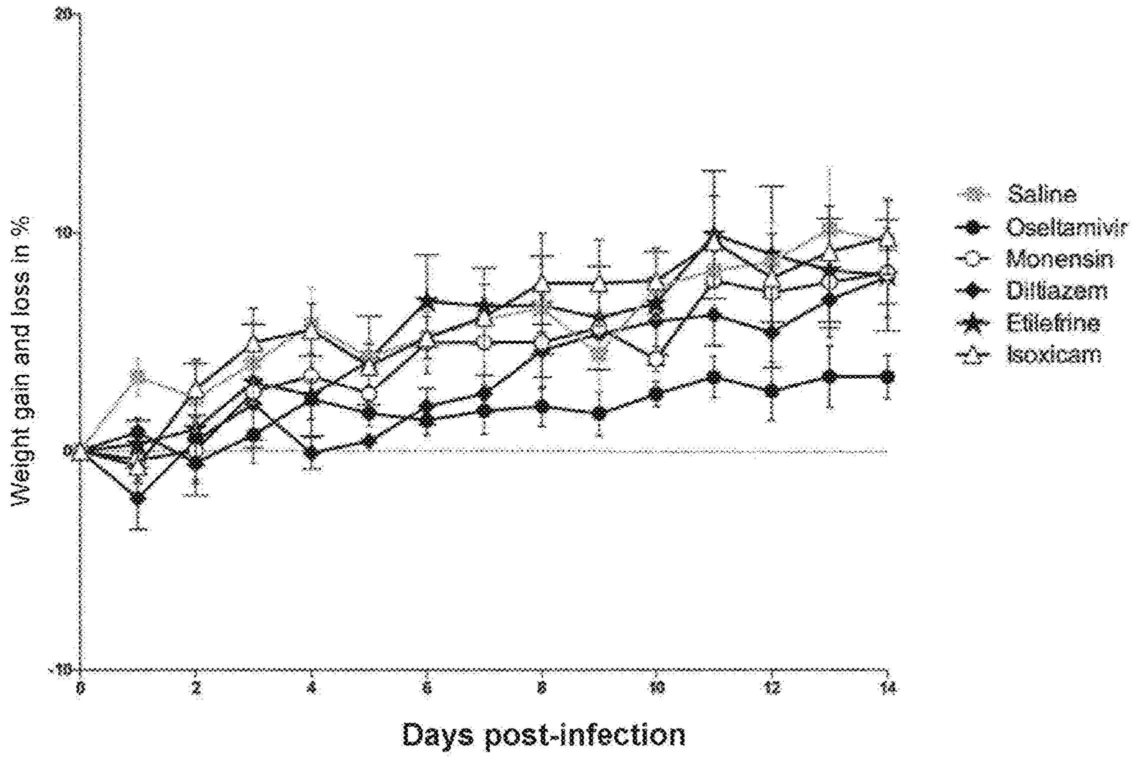
Figure 5A:
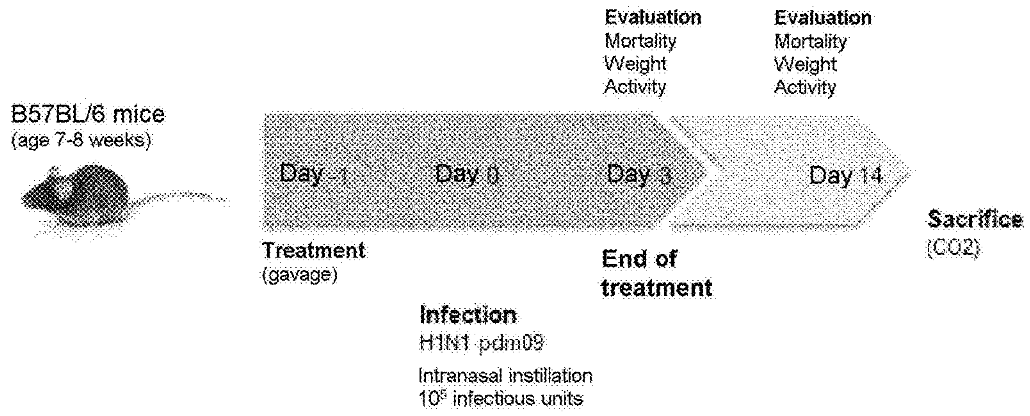
Figure 5B:
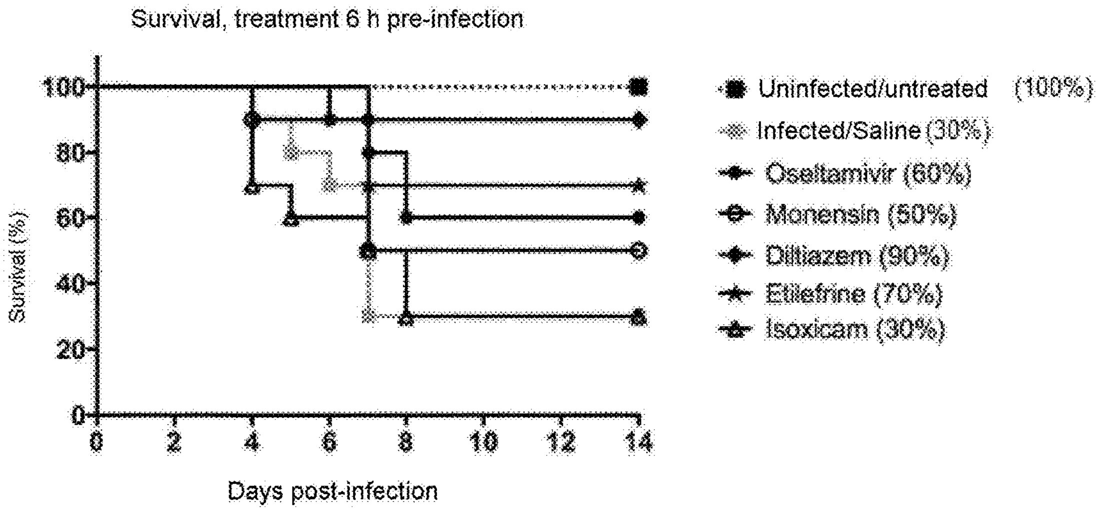
Figure 5C:
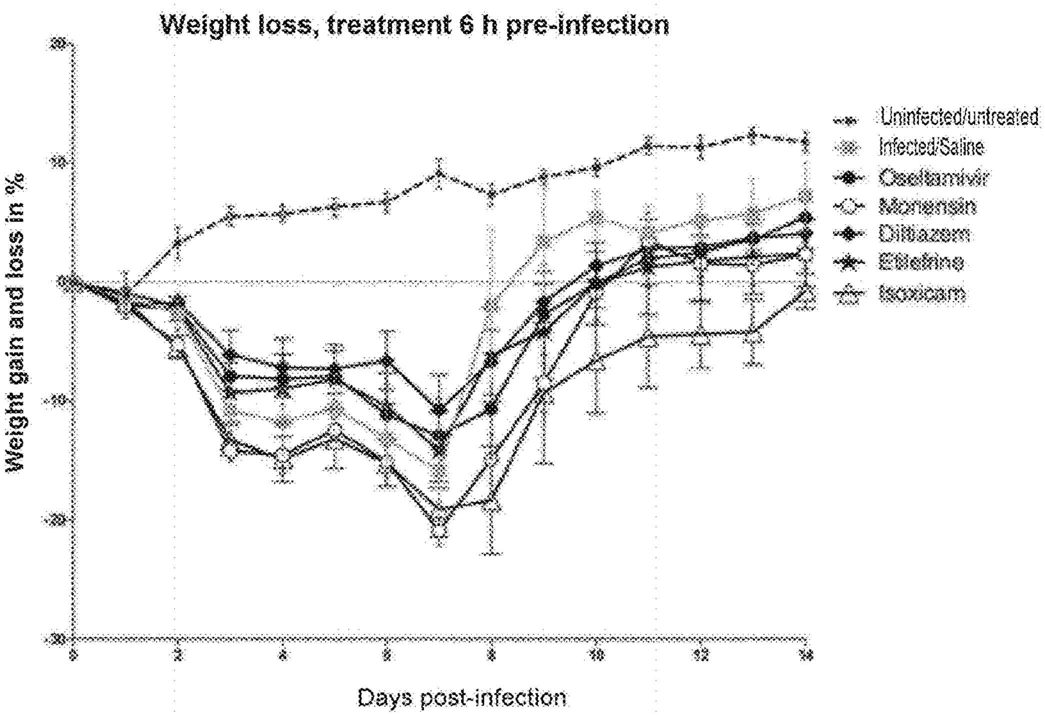
Figure 5D:
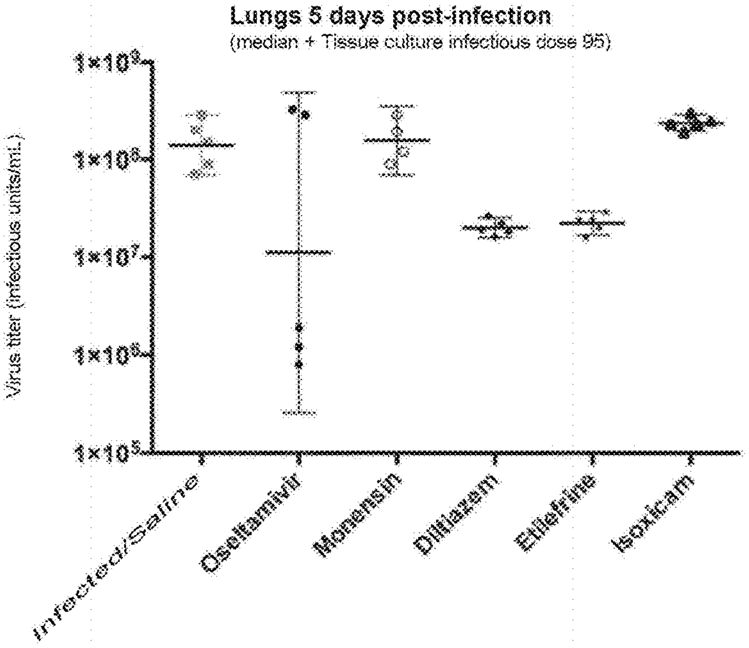
Figure 6A:
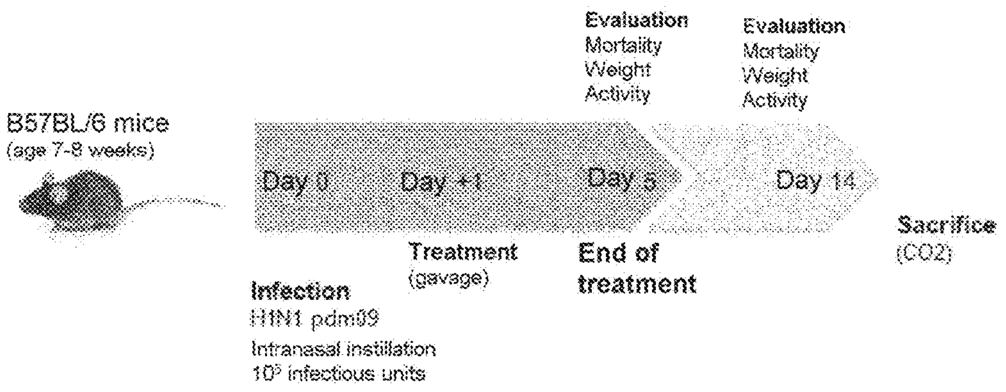
Figure 6B:
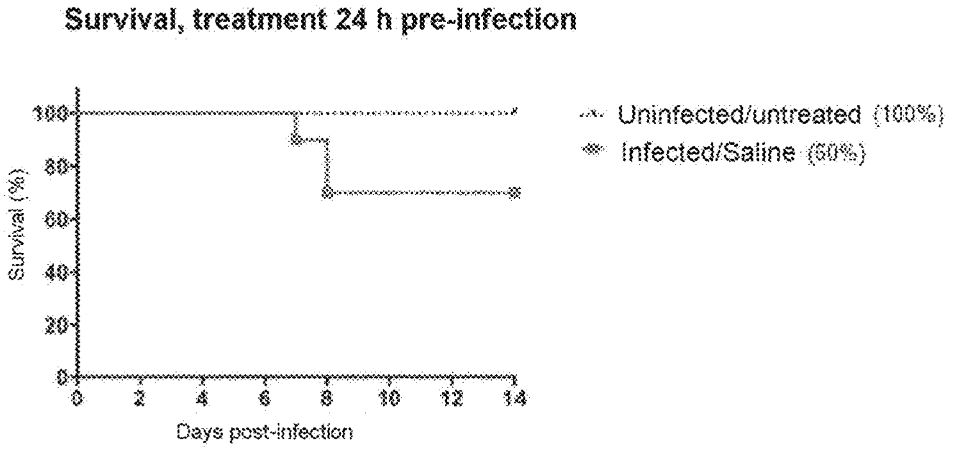
Figure 6C:
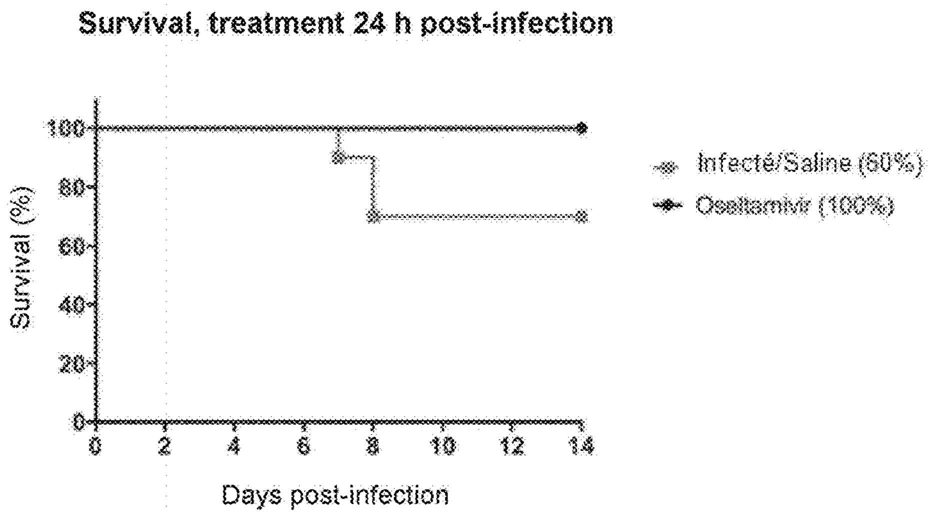
Figure 6D:
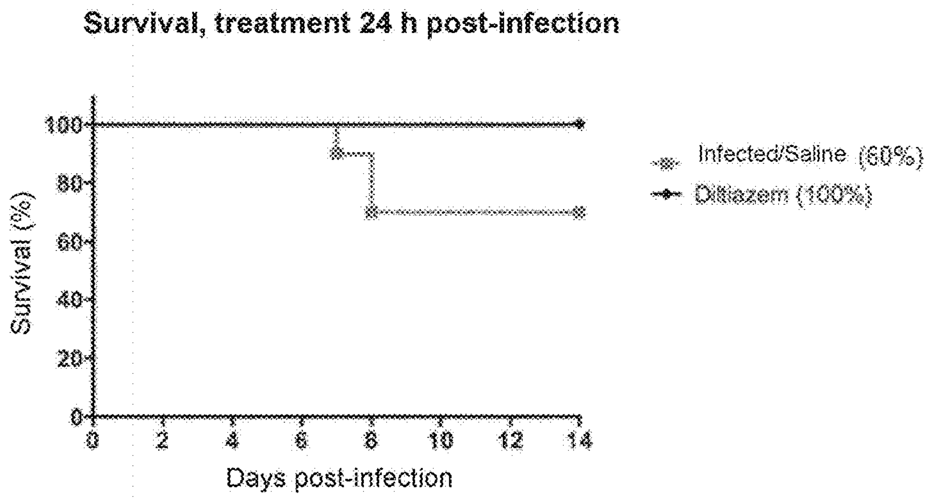
Figure 7A:
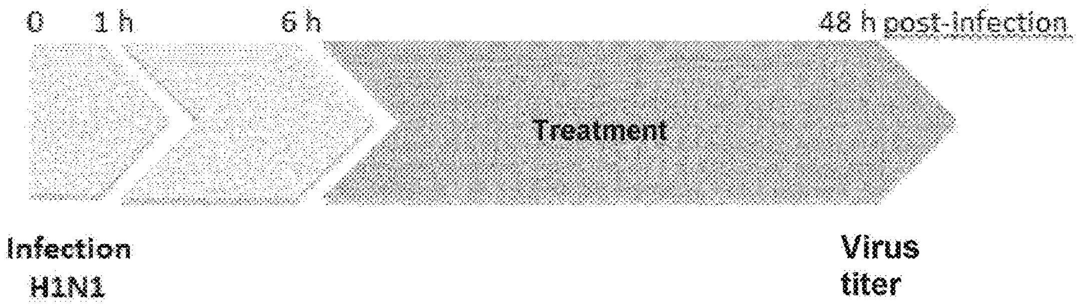
Figure 7B:
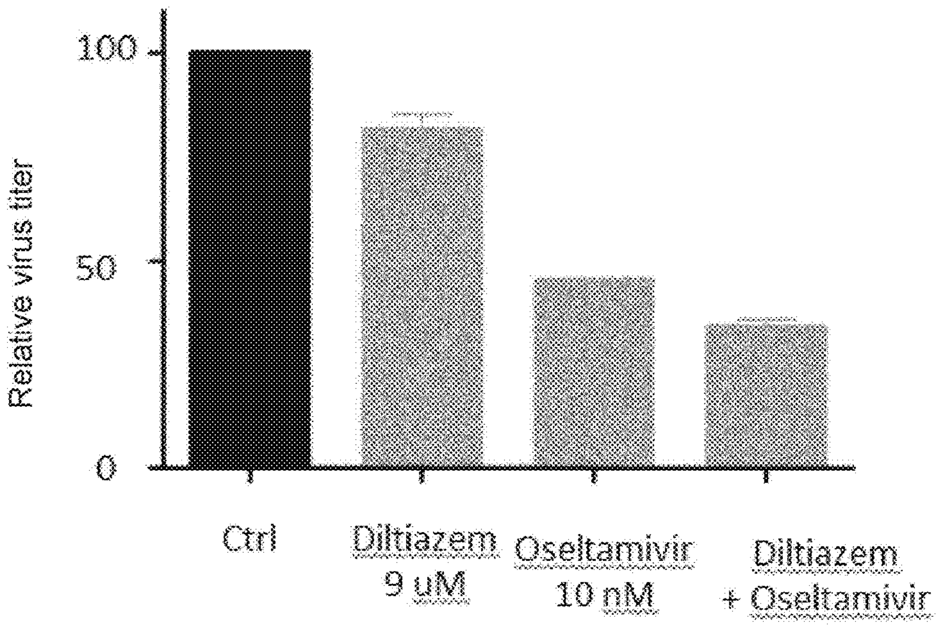
Figure 7C:
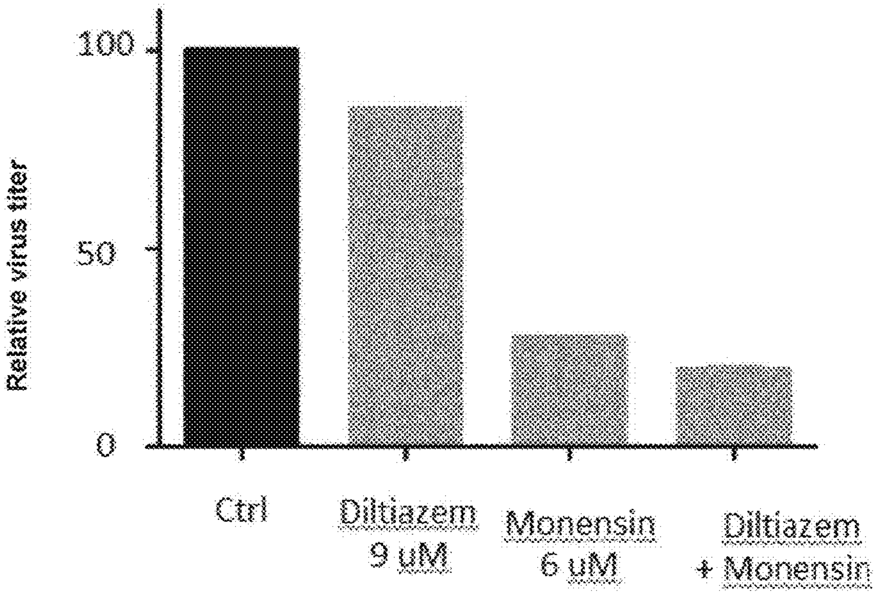

In post-infection treatment conditions of HAE infected with H1N1 pdm09, oseltamivir 1 μM (but not 0.1 μM) significantly decreases virus production of up to 3 log 10, relative to the control value at the peak of viral replication (48 hpi).

A comparable antiviral effect is observed for diltiazem 90 μM but not for diltiazem 9 μM.

Figure 8A:
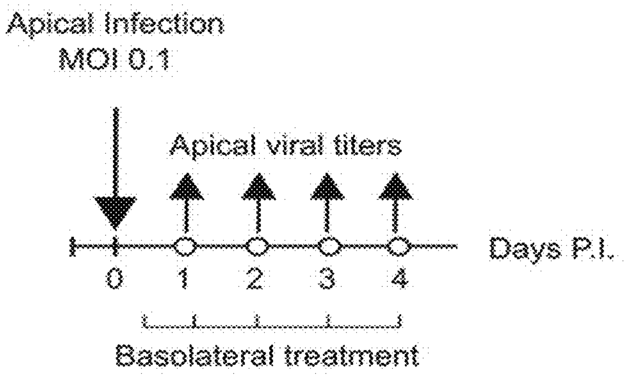
FIGS. 8B shows the results obtained for the single-drug treatments with diltiazem or oseltamivir against infection with influenza H1N1 pdm09.
FIG. 8C shows the results obtained for the diltiazem and oseltamivir combination, against infection with influenza H1N1 pdm09, with two concentrations: 90/1 μM (full grey line) and 9/0.1 μM (dotted grey line).
FIGS. 8D and 8E show the results obtained for the diltiazem and oseltamivir combination against infection with influenza H3N2 or B, respectively.
Figure 8B:
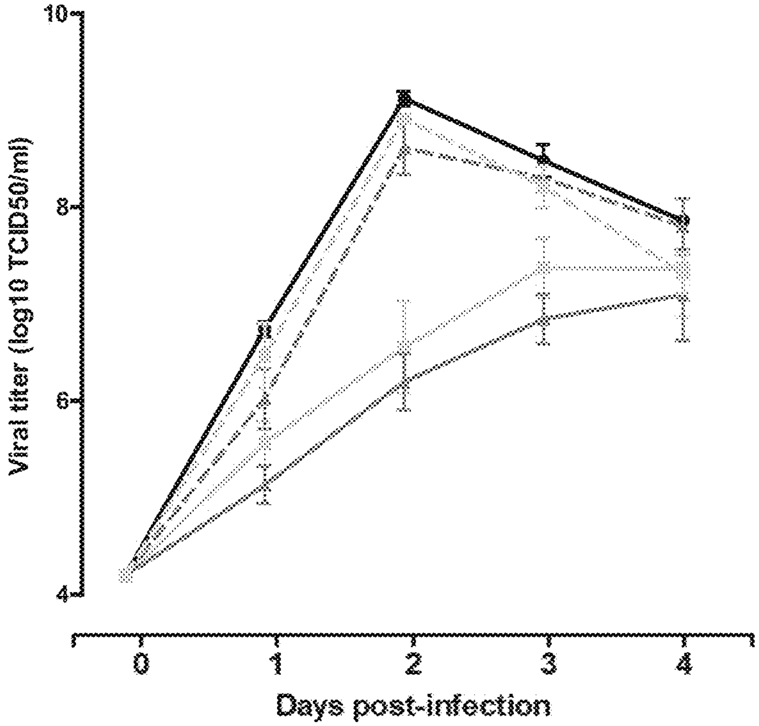
Figure 8C:
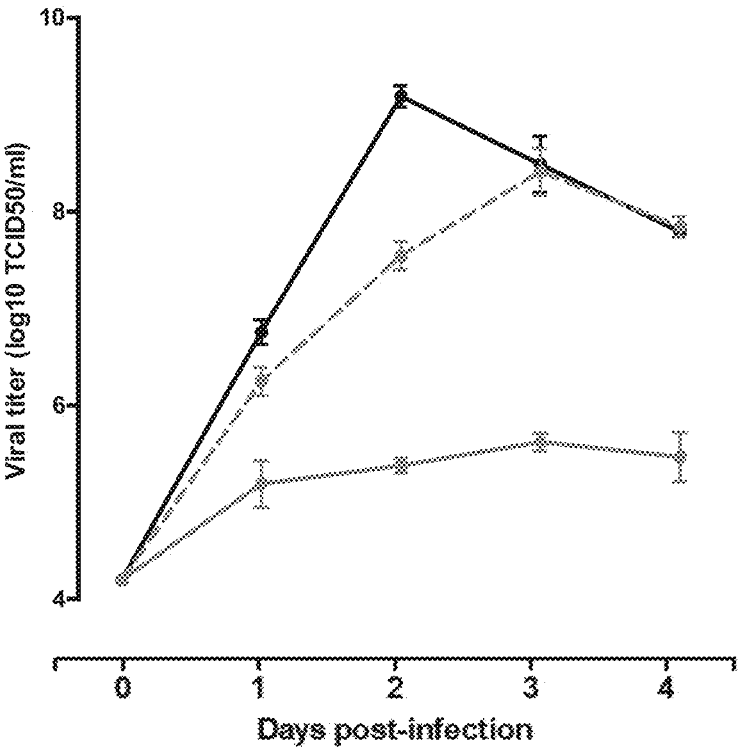
Figure 8D:
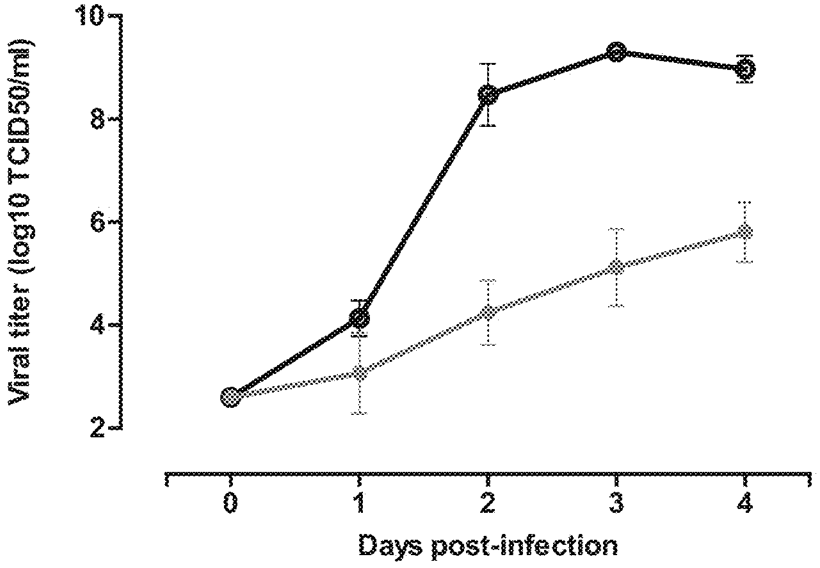
Figure 8E:
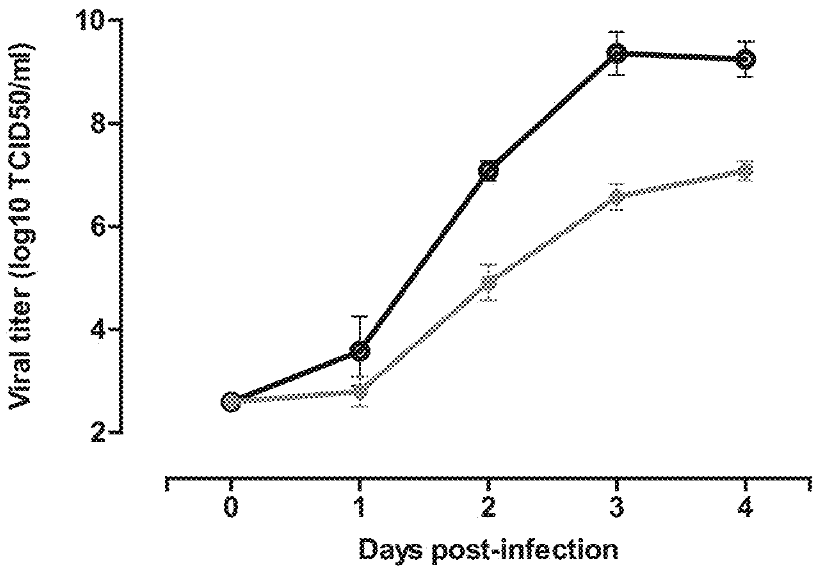

The combination of diltiazem and oseltamivir performs much better than the compounds alone, with an additional 1 log 10 reduction on viral load for the diltiazem 90 μM and oseltamivir 1 μM combination, compared to the respective single-drug treatments (FIG. 8C).

Moreover, the diltiazem 9 μM and oseltamivir 0.1 μM combination induced a >1 log 10 reduction on viral load, compared to the untreated control at post-infection day 2, and to each of the single-drug treatments, which showed no significant antiviral affect at the respective doses. Thus, the effects of oseltamivir are potentiated by the presence of diltiazem (FIG. 8C).

Finally, the diltiazem 90 μM and oseltamivir 1 μM combination also significantly decreased peak viral loads by 4 and 2.5 log 10 TCID50/ml in HAE infected with influenza H3N2 and B, respectively, relative to the untreated control (FIG. 8C).

Example 9. In vitro evaluation of the antiviral effect and synergistic potential of the diltiazem and oseltamivir combination in A549 cells infected with H1N1 pdm09, as calculated using the CompuSyn software (FIG. 9 and TABLE 1).

CompuSyn is a software for general dose-effect analysis and quantitation of synergism and antagonism in drug combinations, by fitting experimental data into the median-effect principle of the mass-action. The determination of dose-response curve-associated parameters such as potency (Dm), shape (m) and fitting (r) for each drug and their combinations enable to calculate synergism, additive effect, or antagonism. (Chou and Martin, 2005; Chou, 2006)

Figures 9A, 9B:
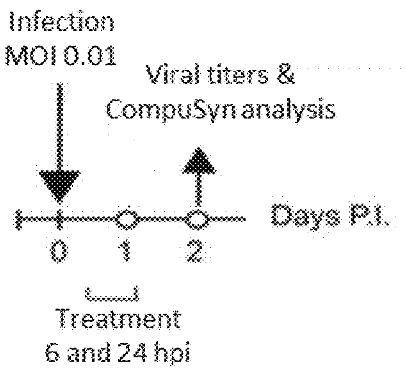

The post-infection A549 cell treatment protocol is shown diagrammatically in FIG. 9A. Cells were infected with H1N1 for 1 hour and treatments at 5 different concentrations (in nM) of each drug were initiated 6 h post-infection and repeated once at 24 hpi. Supernatants were collected at 48 hpi and the effect of the treatments on virus production was measured.

FIG. 9B shows the parameters of the dose-effect curves for single-drug treatments with diltiazem or oseltamivir, and for the diltiazem and oseltamivir combination.

Figure 9C:
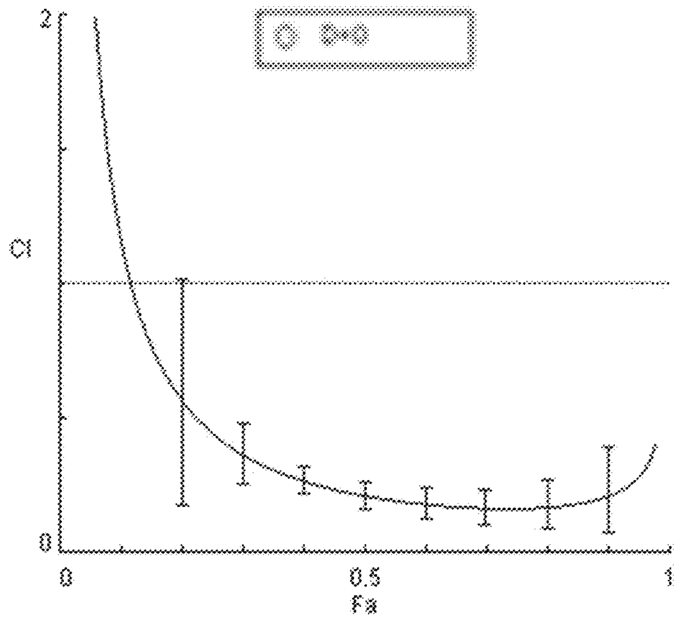

FIG. 9C shows the Combination Index (CI) curve and detailed values for the diltiazem and oseltamivir combination at inhibition levels (Fa) comprised between 50% and 97%.

TABLE 1 summarizes the dose ratios and combination index (CI) of the diltiazem and oseltamivir combination at the highest H1N1 inhibition levels (Fa: 90%, 95% and 97%) in A549 cells, as calculated using the CompuSyn software.

| | Drug/Combo | CI value | Dose Diltiazem | Dose Oseltamivir |
|---|---|---|---|---|
| Data for Fa = 0.90 (90%) | Diltiazem | — | 82393.5 | — |
| | Oseltamivir | — | — | 7507.97 |
| | Dil + Ose | 0.21068 | 15815.6 | 140.583 |
| Data for Fa = 0.95 (95%) | Diltiazem | — | 237259 | — |
| | Oseltamivir | — | — | 62435 |
| | Dil + Ose | 0.28537 | 65495.4 | 582.181 |
| Data for Fa = 0.97 (97%) | Diltiazem | — | 503555 | — |
| | Oseltamivir | — | — | 281813 |
| | Dil + Ose | 0.36317 | 180015 | 1600.13 |

In post-infection treatment conditions of A549 cells infected with H1N1, the dose-response curves for the two single and one combined treatment (at 5 doses each) showed r values superior to 0.9, thus validating the software-assisted CI analysis.

For all the scenarios with viral inhibition (Fa) equal or superior to 50%, the diltiazem and oseltamivir combination shows CI values comprised between 0.16 and 0.36, corresponding to a synergistic (CI 0.3-0.7) or strongly synergistic (CI 0.1-0.3) effect of the drug combination.

REFERENCES

Patents

FR 2 953 410
EP0162320
EP0728751
EP0561861
EP0450705
EP0355395
WO 87/07508
WO 2011/126071
CN102657621
WO 02/094238
U.S. Pat. No. 4,605,552

Scientific literature

Josset L, Textoris J, Loriod B, Ferraris O, Moules V, Lina B, N'guyen C, Diaz J J, Rosa-Calatrava M. "Gene expression signature-based screening identifies new broadly effective influenza A antivirals." PLoS One. 2010 Oct. 4; 5(10).

Terrier O, Josset L, Textoris J, Marcel V, Cartet G, Ferraris O, N'guyen C, Lina B, Diaz J J, Bourdon J C, Rosa-Calatrava M. "Cellular transcriptional profiling in human lung epithelial cells infected by different subtypes of influenza A viruses reveals an overall down-regulation of the host p53 pathway." Virol J. 2011 Jun. 8; 8:285.

Terrier O, Textoris J, Carron C, Marcel V, Bourdon J C, Rosa-Calatrava M. "Host microRNA molecular signatures associated with human H1N1 and H3N2 influenza A viruses reveal an unanticipated antiviral activity for miR-146a." J Gen Virol. 2013 May; 94(Pt 5):985-95.

Chou T C and Martin N. CompuSyn for Drug Combinations: PC Software and User's Guide: A Computer Program for Quantitation of Synergism and Antagonism in Drug Combinations, and the Determination of IC50 and ED50 and LD50 Values, ComboSyn Inc, Paramus, (NJ), 2005. www.combosyn.com Chou T C. Theoretical basis, experimental design, and computerized simulation of synergism and antagonism in drug combination studies. Pharmacol Rev 58:621-681, 2006.

The invention claimed is:

1. A therapeutic method for treating infection with influenza viruses in a human or an animal, wherein the method comprises administration to the human or the animal of a combination of diltiazem and oseltamivir, in a ratio of diltiazem:oseltamivir between 900:1 and 0.9:1.

2. The method according to claim 1, wherein the influenza viruses are selected from type A viruses.

3. The method according to claim 1, wherein the combination is in a dosage form intended for administration by inhalation.

4. The method according to claim 1, further comprising the administration of another antiviral agent.

5. The method according to claim 4, wherein the other antiviral agent has an inhibitory activity on influenza viruses.

6. The method according to claim 5, wherein the other antiviral agent is selected from zanamivir, peramivir, amantadine, rimantadine, ribavirin and arbidol.

7. The method according to claim 1, further comprising the administration of at least one antibacterial agent.

8. A method for treating infection with influenza viruses, comprising the simultaneous, separate or sequential administration of diltiazem and oseltamivir, in a ratio of diltiazem:oseltamivir between 900:1 and 0.9:1.

9. The method according to claim 8, further comprising the simultaneous, separate or sequential administration of at least one antibacterial agent.

10. The method according to claim 2, wherein the type A virus is selected from the group consisting of H1N1, H2N2, H3N2, H5N1, H7N7 and H7N9 subtypes.

* * * * *